US009949730B2

(12) United States Patent
Hart et al.

(10) Patent No.: US 9,949,730 B2
(45) Date of Patent: Apr. 24, 2018

(54) CIRCUMFERENTIAL WOUND RETRACTION WITH SUPPORT AND GUIDANCE STRUCTURES

(71) Applicant: Applied Medical Resources Corporation, Rancho Santa Margarita, CA (US)

(72) Inventors: Charles C. Hart, Rancho Santa Margarita, CA (US); Boun Pravong, Rancho Santa Margarita, CA (US); Kennii Pravongviengkham, Rancho Santa Margarita, CA (US); Eduardo Bolanos, Rancho Santa Margarita, CA (US); Tina Talwar, Rancho Santa Margarita, CA (US); Tracy Breslin, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 14/950,261

(22) Filed: Nov. 24, 2015

(65) Prior Publication Data

US 2016/0220240 A1 Aug. 4, 2016

Related U.S. Application Data

(60) Provisional application No. 62/084,435, filed on Nov. 25, 2014.

(51) Int. Cl.

*A61B 17/02* (2006.01)
*A61B 17/34* (2006.01)

(Continued)

(52) U.S. Cl.

CPC ........ *A61B 17/0218* (2013.01); *A61B 1/0684* (2013.01); *A61B 1/07* (2013.01);

(Continued)

(58) Field of Classification Search

CPC ................................................ A61B 17/0218

See application file for complete search history.

(56) References Cited

U.S. PATENT DOCUMENTS 52,014 A 1/1866 Bartlett
202,813 A 4/1878 Hall (Continued)

FOREIGN PATENT DOCUMENTS

CN 202751416 U 2/2013
DE 26 05 148 A1 8/1977

(Continued)

OTHER PUBLICATIONS

The International Bureau of WIPO, International Preliminary Report on Patentability for International Application No. PCT/US2015/062326, titled "Circumferential Wound Retraction with Support and Guidance Structures," dated Jun. 8, 2017, 16 pgs.

(Continued)

*Primary Examiner* — Ellen C Hammond
*Assistant Examiner* — Stuart S Bray
(74) *Attorney, Agent, or Firm* — Cynthia A. Bonner

(57) ABSTRACT

Embodiments of a circumferential retractor having an attached supporting, manipulating or positioning tool are described. The retractor optionally includes a sealing member associated with an external member of the retractor and an external support structure that may be used with the retractor and positioning tool as needed.

7 Claims, 41 Drawing Sheets

153
393
90
91
393
154
393

(51) Int. Cl.
*A61B 1/06* (2006.01)
*A61B 1/07* (2006.01)
*A61B 17/00* (2006.01)
*A61B 90/30* (2016.01)
*A61B 90/57* (2016.01)
*A61B 90/00* (2016.01)

(52) U.S. Cl.
CPC ...... *A61B 17/0293* (2013.01); *A61B 17/3423* (2013.01); *A61B 17/3474* (2013.01); *A61B 2017/00477* (2013.01); *A61B 2017/00557* (2013.01); *A61B 2017/00796* (2013.01); *A61B 2017/00862* (2013.01); *A61B 2017/00871* (2013.01); *A61B 2017/0225* (2013.01); *A61B 2017/3429* (2013.01); *A61B 2017/3441* (2013.01); *A61B 2017/3445* (2013.01); *A61B 2017/3466* (2013.01); *A61B 2017/3486* (2013.01); *A61B 2017/3492* (2013.01); *A61B 2090/306* (2016.02); *A61B 2090/309* (2016.02); *A61B 2090/3618* (2016.02); *A61B 2090/571* (2016.02)

(56) References Cited

U.S. PATENT DOCUMENTS 447,761 A 3/1891 Clough
558,364 A 4/1896 Doolittle
758,535 A 4/1904 Howden
929,583 A 7/1909 Gibbs
1,056,966 A 3/1913 Belding
1,157,202 A 10/1915 Bates et al.
1,221,123 A 4/1917 Westhaver
1,242,972 A 10/1917 Petit
1,598,284 A 8/1926 Kinney
1,690,995 A 11/1928 Pratt
1,180,466 A 6/1931 Deutsch
1,810,466 A 6/1931 Deutsch
2,219,564 A 10/1940 Reyniers
2,305,289 A 12/1942 Coburg
2,313,164 A 3/1943 Wa Nelson
2,478,586 A 8/1949 Krapp
2,669,991 A 2/1954 Curutchet
2,695,608 A 11/1954 Gibbon
2,812,758 A 11/1957 Blumenschein
2,835,253 A 5/1958 Borgeson
2,853,075 A 9/1958 Hoffman et al.
3,039,468 A 6/1962 Price
3,057,350 A 10/1962 Cowley
3,111,943 A 11/1963 Orndorff
3,129,706 A 4/1964 Reynolds, Jr.
3,195,934 A 7/1965 Parrish
3,244,169 A 4/1966 Baxter
3,253,594 A 5/1966 Matthews et al.
3,313,299 A 4/1967 Spademan
3,329,390 A 7/1967 Hulsey
3,332,417 A 7/1967 Blanford et al.
3,347,226 A 10/1967 Harrower
3,347,227 A 10/1967 Harrower
3,397,692 A 8/1968 Creager, Jr. et al.
3,402,710 A 9/1968 Paleschuck
3,416,520 A 12/1968 Creager, Jr.
3,447,533 A 6/1969 Spicer
3,522,800 A 8/1970 Lesser
3,523,534 A 8/1970 Nolan
3,553,862 A 1/1971 Hamu
3,570,475 A 3/1971 Weinstein
3,656,485 A 4/1972 Robertson
3,685,786 A 8/1972 Woodson
3,703,896 A 11/1972 Nuwayser
3,717,151 A 2/1973 Collett
3,717,883 A 2/1973 Mosher
3,729,006 A 4/1973 Wilder et al.
3,729,027 A 4/1973 Bare
3,729,045 A 4/1973 MacDonald
3,762,080 A 10/1973 Poole
3,774,596 A 11/1973 Cook
3,782,370 A 1/1974 McDonald
3,788,318 A 1/1974 Kim et al.
3,789,852 A 2/1974 Kim et al.
3,797,478 A 3/1974 Walsh et al.
3,799,166 A 3/1974 Marsan
3,807,393 A 4/1974 McDonald
3,828,764 A 8/1974 Jones
3,831,583 A 8/1974 Edmunds et al.
3,841,332 A 10/1974 Treacle
3,850,172 A 11/1974 Cazalis
3,853,126 A 12/1974 Schulte
3,853,127 A 12/1974 Spademan
3,856,021 A 12/1974 McIntosh
3,860,274 A 1/1975 Ledstrom et al.
3,861,416 A 1/1975 Wichterle
3,863,639 A 2/1975 Kleaveland
3,907,389 A 9/1975 Cox et al.
3,915,171 A 10/1975 Shermeta
3,965,890 A 6/1976 Gauthier
3,970,089 A 7/1976 Saice
3,996,623 A 12/1976 Kaster
4,000,739 A 1/1977 Stevens
4,016,884 A 4/1977 Kwan-Gett
4,024,872 A 5/1977 Muldoon
4,030,500 A 6/1977 Ronnquist
4,043,328 A 8/1977 Cawood, Jr. et al.
4,069,913 A 1/1978 Harrigan
4,082,005 A 4/1978 Erdley
4,083,370 A 4/1978 Taylor
4,096,853 A 6/1978 Weigand
4,112,932 A 9/1978 Chiulli
4,117,847 A 10/1978 Clayton
4,130,113 A 12/1978 Graham
4,141,364 A 2/1979 Schultze
4,177,814 A 12/1979 Knepshield et al.
4,183,357 A 1/1980 Bentley et al.
4,187,849 A 2/1980 Stim
4,188,945 A 2/1980 Wenander
4,189,880 A 2/1980 Ballin
4,217,664 A 8/1980 Faso
4,222,126 A 9/1980 Boretos et al.
4,228,792 A 10/1980 Rhys-Davies
4,239,036 A 12/1980 Krieger
4,240,411 A 12/1980 Hosono
4,253,201 A 3/1981 Ross et al.
4,254,973 A 3/1981 Banjamin
4,306,562 A 12/1981 Osborne
4,321,915 A 3/1982 Leighton
4,331,138 A 5/1982 Jessen
4,338,934 A 7/1982 Spademan
4,338,937 A 7/1982 Lerman
4,367,728 A 1/1983 Mutke
4,369,284 A 1/1983 Chen
4,399,816 A 8/1983 Spangler
4,402,683 A 9/1983 Kopman
4,411,659 A 10/1983 Jensen et al.
4,421,296 A 12/1983 Stephens
4,424,833 A 1/1984 Spector et al.
4,428,364 A 1/1984 Bartolo
4,430,081 A 2/1984 Timmermans
4,434,791 A 3/1984 Darnell
4,436,519 A 3/1984 O'Neill
4,454,873 A 6/1984 Laufenberg et al.
4,473,067 A 9/1984 Schiff
4,475,548 A 10/1984 Muto
4,485,490 A 12/1984 Akers et al.
4,488,877 A 12/1984 Klein
4,508,355 A 4/1985 Ditcher
4,543,088 A 9/1985 Bootman et al.
4,550,713 A 11/1985 Hyman
4,553,537 A 11/1985 Rosenberg
4,555,242 A 11/1985 Saudagar
4,556,996 A 12/1985 Wallace
4,601,710 A 7/1986 Moll
4,610,665 A 9/1986 Matsumoto et al.
4,626,245 A 12/1986 Weinstein

(56) References Cited

U.S. PATENT DOCUMENTS 4,634,424 A 1/1987 O'Boyle
4,634,432 A 1/1987 Kocak
4,644,951 A 2/1987 Bays
4,649,904 A 3/1987 Krauter
4,653,476 A 3/1987 Bonnet
4,654,030 A 3/1987 Moll et al.
4,655,752 A 4/1987 Honkanen et al.
4,673,393 A 6/1987 Suzuki et al.
4,673,394 A 6/1987 Fenton
4,691,942 A 9/1987 Ford
4,714,749 A 12/1987 Hughes et al.
4,738,666 A 4/1988 Fuqua
4,755,170 A 7/1988 Golden
4,760,933 A 8/1988 Christner et al.
4,776,843 A 10/1988 Martinez et al.
4,777,943 A 10/1988 Chvapil
4,784,646 A 11/1988 Feingold
4,796,629 A 1/1989 Grayzel
4,798,594 A 1/1989 Hillstead
4,802,694 A 2/1989 Vargo
4,808,168 A 2/1989 Warring
4,809,679 A 3/1989 Shimonaka et al.
4,828,554 A 5/1989 Griffin
4,842,931 A 6/1989 Zook
4,848,575 A 7/1989 Nakamura et al.
4,856,502 A 8/1989 Ersfeld et al.
4,863,430 A 9/1989 Klyce et al.
4,863,438 A 9/1989 Gauderer et al.
4,889,107 A 12/1989 Kaufman
4,895,565 A 1/1990 Hillstead
4,897,081 A 1/1990 Poirier
4,903,710 A 2/1990 Jessamine et al.
4,911,974 A 3/1990 Shimizu et al.
4,915,132 A 4/1990 Hodge et al.
4,926,882 A 5/1990 Lawrence
4,929,235 A 5/1990 Merry et al.
4,944,732 A 7/1990 Russo
4,950,222 A 8/1990 Scott et al.
4,950,223 A 8/1990 Silvanov
4,984,564 A 1/1991 Yuen
4,991,593 A 2/1991 LeVahn
4,998,538 A 3/1991 Charowsky et al.
5,000,745 A 3/1991 Guest et al.
5,009,224 A 4/1991 Cole
5,015,228 A 5/1991 Columbus et al.
5,019,101 A 5/1991 Purkait et al.
5,026,366 A 6/1991 Leckrone
5,037,379 A 8/1991 Clayman et al.
5,041,095 A 8/1991 Littrell
5,045,070 A 9/1991 Grodecki et al.
D320,658 S 10/1991 Quigley et al.
5,071,411 A 12/1991 Hillstead
5,073,169 A 12/1991 Raiken
5,074,878 A 12/1991 Bark et al.
5,082,005 A 1/1992 Kaldany
5,086,763 A 2/1992 Hathman
5,092,846 A 3/1992 Nishijima et al.
5,104,389 A 4/1992 Deem
5,108,420 A 4/1992 Marks
5,125,396 A 6/1992 Ray
5,125,897 A 6/1992 Quinn et al.
5,127,626 A 7/1992 Hilal et al.
5,129,885 A 7/1992 Green et al.
5,141,498 A 8/1992 Christian
5,149,327 A 9/1992 Oshiyama
5,156,617 A 10/1992 Reid
5,158,553 A 10/1992 Berry et al.
5,159,921 A 11/1992 Hoover
5,161,773 A 11/1992 Tower
5,167,636 A 12/1992 Clement
5,167,637 A 12/1992 Okada et al.
5,176,648 A 1/1993 Holmes et al.
5,176,662 A 1/1993 Bartholomew et al.
5,176,697 A 1/1993 Hasson et al.
5,178,162 A 1/1993 Bose
5,180,365 A 1/1993 Ensminger et al.
5,183,471 A 2/1993 Wilk
5,188,595 A 2/1993 Jacobi
5,188,607 A 2/1993 Wu
5,192,301 A 3/1993 Kamiya et al.
5,197,955 A 3/1993 Stephens et al.
5,207,656 A 5/1993 Kranys
5,209,737 A 5/1993 Rirchart et al.
5,211,370 A 5/1993 Powers
5,211,633 A 5/1993 Stouder, Jr.
5,213,114 A 5/1993 Bailey, Jr.
5,226,890 A 7/1993 Ianniruberto et al.
5,234,455 A 8/1993 Mulhollan
5,241,968 A 9/1993 Slater
5,242,400 A 9/1993 Buelna
5,242,409 A 9/1993 Buelna
5,242,412 A 9/1993 Blake, III
5,242,415 A 9/1993 Kantrowitz et al.
5,248,304 A 9/1993 Vigdorchik et al.
5,256,150 A 10/1993 Quiachon et al.
5,257,973 A 11/1993 Villasuso
5,257,975 A 11/1993 Foshee
5,259,366 A 11/1993 Reydel et al.
5,261,883 A 11/1993 Hood et al.
5,262,468 A 11/1993 Chen
5,263,922 A 11/1993 Soya et al.
5,269,763 A 12/1993 Boehmer et al.
5,269,772 A 12/1993 Wilk
5,273,449 A 12/1993 Mattis et al.
5,273,545 A 12/1993 Hunt et al.
D343,236 S 1/1994 Quigley et al.
5,279,575 A 1/1994 Sugarbaker
5,290,310 A 3/1994 Makower et al.
D346,022 S 4/1994 Quigley et al.
5,299,582 A 4/1994 Potts
5,300,034 A 4/1994 Behnke
5,300,035 A 4/1994 Clement
5,300,036 A 4/1994 Mueller et al.
5,303,486 A 4/1994 Dell
5,308,336 A 5/1994 Hart et al.
5,309,896 A 5/1994 Moll et al.
5,312,391 A 5/1994 Wilk
5,314,417 A 5/1994 Stephens et al.
5,316,541 A 5/1994 Fischer
5,320,611 A 6/1994 Bonutti et al.
5,330,437 A 7/1994 Durman
5,330,486 A 7/1994 Wilk
5,330,497 A 7/1994 Freitas et al.
5,331,975 A 7/1994 Bonutti
5,334,143 A 8/1994 Carroll
5,334,646 A 8/1994 Chen
5,336,192 A 8/1994 Palestrant
5,336,708 A 8/1994 Chen
5,338,313 A 8/1994 Mollenauer et al.
5,342,315 A 8/1994 Rowe et al.
5,342,385 A 8/1994 Norelli et al.
5,350,364 A 9/1994 Stephens et al.
5,353,786 A 10/1994 Wilk
5,354,280 A 10/1994 Haber et al.
5,360,417 A 11/1994 Gravener et al.
5,364,345 A 11/1994 Lowery et al.
5,364,372 A 11/1994 Danks et al.
5,366,446 A 11/1994 Tal et al.
5,366,473 A 11/1994 Winston et al.
5,366,478 A 11/1994 Brinkerhoff et al.
5,368,545 A 11/1994 Schaller et al.
5,375,588 A 12/1994 Yoon
5,380,288 A 1/1995 Hart et al.
5,383,861 A 1/1995 Hempel et al.
5,385,552 A 1/1995 Haber et al.
5,385,553 A 1/1995 Hart et al.
5,385,560 A 1/1995 Wulf
5,389,080 A 2/1995 Yoon
5,389,081 A 2/1995 Castro
5,391,153 A 2/1995 Haber et al.
5,391,156 A 2/1995 Hildwein et al.
5,395,367 A 3/1995 Wilk
5,400,773 A * 3/1995 Zhu .................... A61B 17/0218
600/205

(56) References Cited

U.S. PATENT DOCUMENTS 5,403,264 A 4/1995 Wohlers et al.
5,403,336 A 4/1995 Kieturakis et al.
5,407,433 A 4/1995 Loomas
5,411,483 A 5/1995 Loomas
5,413,571 A 5/1995 Katsaros et al.
5,423,848 A 6/1995 Washizuka et al.
5,429,609 A 7/1995 Yoon
5,431,676 A 7/1995 Durdal et al.
5,437,683 A 8/1995 Neumann et al.
5,439,455 A 8/1995 Kieturakis et al.
5,441,486 A 8/1995 Yoon
5,443,452 A 8/1995 Hart et al.
5,454,365 A 10/1995 Bonutti
5,456,284 A 10/1995 Ryan et al.
5,460,170 A 10/1995 Hammerslag
5,460,616 A 10/1995 Weinstein et al.
5,468,248 A 11/1995 Chin et al.
5,476,475 A 12/1995 Gadberry
5,480,410 A 1/1996 Cuschieri et al.
5,486,426 A 1/1996 McGee et al.
5,490,843 A 2/1996 Hildwein et al.
5,492,304 A 2/1996 Smith et al.
5,496,280 A 3/1996 Vandenbroek et al.
5,503,112 A 4/1996 Luhman et al.
5,507,758 A 4/1996 Thomason et al.
5,508,334 A 4/1996 Chen
5,511,564 A 4/1996 Wilk
5,514,109 A 5/1996 Mollenauer et al.
5,514,133 A 5/1996 Golub et al.
5,514,153 A 5/1996 Bonutti
5,518,278 A 5/1996 Sampson
5,520,632 A 5/1996 Leveen
5,522,791 A 6/1996 Leyva
5,522,824 A 6/1996 Ashby
5,524,644 A 6/1996 Crook
5,526,536 A 6/1996 Cartmill
5,531,758 A 7/1996 Uschold et al.
5,538,509 A 7/1996 Dunlap et al.
5,540,648 A 7/1996 Yoon
5,540,711 A 7/1996 Kieturakis et al.
5,545,150 A 8/1996 Danks et al.
5,545,179 A 8/1996 Williamson, IV
5,549,563 A 8/1996 Kronner
5,549,637 A 8/1996 Crainich
5,554,124 A 9/1996 Alvarado
5,555,653 A 9/1996 Morgan
5,562,632 A 10/1996 Davila et al.
5,562,677 A 10/1996 Hildwein et al.
5,562,688 A 10/1996 Riza
5,571,115 A 11/1996 Nicholas
5,571,137 A 11/1996 Marlow et al.
5,575,799 A 11/1996 Bolanos et al.
5,577,993 A 11/1996 Zhu et al.
5,578,048 A 11/1996 Pasqualucci et al.
5,580,344 A 12/1996 Hasson
5,584,850 A 12/1996 Hart et al.
5,601,579 A 2/1997 Semertzides
5,601,581 A 2/1997 Fogarty et al.
5,603,702 A 2/1997 Smith et al.
5,607,443 A 3/1997 Kieturakis et al.
5,620,415 A 4/1997 Lucey et al.
5,620,420 A 4/1997 Kriesel
5,628,732 A 5/1997 Antoon, Jr. et al.
5,632,284 A 5/1997 Graether
5,632,979 A 5/1997 Goldberg et al.
5,634,911 A 6/1997 Hermann et al.
5,634,936 A 6/1997 Linden et al.
5,634,937 A 6/1997 Mollenauer et al.
5,636,645 A 6/1997 Ou
5,640,977 A 6/1997 Leahy et al.
5,643,301 A 7/1997 Mollenauer
5,649,550 A 7/1997 Crook
5,651,771 A 7/1997 Tangherlini et al.
5,653,705 A 8/1997 de la Torre et al.
5,657,963 A 8/1997 Hinchliffe et al.
5,658,272 A 8/1997 Hasson
5,658,306 A 8/1997 Kieturakis
5,662,615 A 9/1997 Blake, III
5,672,168 A 9/1997 de la Torre et al.
5,681,341 A 10/1997 Lunsford et al.
5,683,378 A 11/1997 Christy
5,685,826 A * 11/1997 Bonutti .............. A61B 17/0218 600/204
5,685,854 A 11/1997 Green et al.
5,685,857 A 11/1997 Negus et al.
5,697,914 A 12/1997 Brimhall
5,707,703 A 1/1998 Rothrum et al.
5,709,664 A 1/1998 Vandenbroek et al.
5,713,858 A 2/1998 Heruth et al.
5,713,869 A 2/1998 Morejon
5,715,548 A * 2/1998 Weismiller ........... A61G 7/0527 5/611
5,720,730 A 2/1998 Blake, III
5,725,536 A 3/1998 Oberlin et al.
5,728,103 A 3/1998 Picha et al.
5,730,748 A 3/1998 Fogarty et al.
5,735,791 A 4/1998 Alexander et al.
5,738,628 A 4/1998 Sierocuk et al.
5,741,234 A 4/1998 Aboul-Hosn
5,741,298 A 4/1998 MacLeod
5,743,884 A 4/1998 Hasson et al.
5,749,882 A 5/1998 Hart et al.
5,753,150 A 5/1998 Martin et al.
5,755,660 A 5/1998 Tyagi
5,760,117 A 6/1998 Chen
5,769,783 A 6/1998 Fowler
5,782,812 A 7/1998 Hart et al.
5,782,817 A 7/1998 Franzel et al.
5,782,859 A 7/1998 Nicholas et al.
5,788,676 A 8/1998 Yoon
5,792,119 A 8/1998 Marx
5,794,528 A 8/1998 Gronig et al.
5,795,290 A 8/1998 Bridges
5,803,919 A 9/1998 Hart et al.
5,803,921 A 9/1998 Bonadio
5,803,923 A 9/1998 Singh-Derewa et al.
5,807,350 A 9/1998 Diaz
5,810,712 A 9/1998 Dunn
5,810,721 A 9/1998 Mueller et al.
5,813,409 A 9/1998 Leahy et al.
5,814,026 A 9/1998 Yoon
5,817,062 A 10/1998 Flom et al.
5,819,375 A 10/1998 Kastner
5,820,555 A 10/1998 Watkins, III et al.
5,820,600 A 10/1998 Carlson et al.
5,830,191 A 11/1998 Hildwein et al.
5,832,925 A 11/1998 Rothrum
5,836,871 A 11/1998 Wallace et al.
5,841,298 A 11/1998 Huang
5,842,971 A 12/1998 Yoon
5,848,992 A 12/1998 Hart et al.
5,853,395 A 12/1998 Crook et al.
5,853,417 A 12/1998 Fogarty et al.
5,857,461 A 1/1999 Levitsky et al.
5,860,995 A 1/1999 Berkelaar
5,865,728 A 2/1999 Moll et al.
5,865,729 A 2/1999 Meehan et al.
5,865,807 A 2/1999 Blake, III
5,865,817 A 2/1999 Moenning et al.
5,871,474 A 2/1999 Hermann et al.
5,876,413 A 3/1999 Fogarty et al.
5,879,368 A 3/1999 Hoskin et al.
5,882,344 A 3/1999 Strouder, Jr.
5,884,639 A 3/1999 Chen
5,894,843 A 4/1999 Benetti et al.
5,895,377 A 4/1999 Smith et al.
5,899,208 A 5/1999 Bonadio
5,899,913 A 5/1999 Fogarty et al.
5,904,703 A 5/1999 Gilson
5,906,577 A 5/1999 Beane et al.
5,913,847 A 6/1999 Yoon
5,916,198 A 6/1999 Dillow
5,916,232 A 6/1999 Hart
5,919,476 A 7/1999 Fischer et al.

(56) References Cited

U.S. PATENT DOCUMENTS 5,931,832 A 8/1999 Jensen
5,947,922 A 9/1999 MacLeod
5,951,467 A 9/1999 Picha et al.
5,951,588 A 9/1999 Moenning
5,957,888 A 9/1999 Hinchiffe et al.
5,957,913 A 9/1999 de la Torre et al.
5,961,539 A 10/1999 Northrup, III et al.
5,962,572 A 10/1999 Chen
5,964,781 A 10/1999 Mollenauer et al.
5,976,174 A 11/1999 Ruiz
5,989,232 A 11/1999 Yoon
5,989,233 A 11/1999 Yoon
5,989,266 A 11/1999 Foster
5,993,471 A 11/1999 Riza et al.
5,993,485 A 11/1999 Beckers
5,993,839 A 11/1999 Mixon
5,994,450 A 11/1999 Pearce
5,997,515 A 12/1999 de la Torre et al.
6,004,303 A 12/1999 Peterson
6,010,494 A 1/2000 Schafer et al.
6,017,355 A 1/2000 Hessel et al.
6,018,094 A 1/2000 Fox
6,024,736 A 2/2000 de la Torre et al.
6,025,067 A 2/2000 Fay
6,033,426 A 3/2000 Kaji
6,033,428 A 3/2000 Sardella
6,035,559 A 3/2000 Freed et al.
6,042,573 A 3/2000 Lucey
6,045,535 A 4/2000 Ben Nun
6,048,309 A 4/2000 Flom et al.
6,050,871 A 4/2000 Chen
6,053,934 A 4/2000 Andrews et al.
6,059,816 A 5/2000 Moenning
6,065,166 A * 5/2000 Sharrock ................ A61G 7/065 5/630
6,066,117 A 5/2000 Fox et al.
6,068,639 A 5/2000 Fogarty et al.
6,076,560 A 6/2000 Stähle et al.
6,077,288 A 6/2000 Shimomura
6,086,603 A 7/2000 Termin et al.
6,090,043 A 7/2000 Austin et al.
6,099,506 A 8/2000 Macoviak et al.
6,110,154 A 8/2000 Shimomura et al.
6,123,689 A 9/2000 To
6,142,935 A 11/2000 Flom et al.
6,142,936 A 11/2000 Beane et al.
6,149,642 A 11/2000 Gerhart et al.
6,150,608 A 11/2000 Wambeke et al.
6,154,991 A 12/2000 Duncan et al.
6,159,182 A 12/2000 Davis
6,162,172 A 12/2000 Cosgrove et al.
6,162,196 A 12/2000 Hart et al.
6,162,206 A 12/2000 Bindokas
6,163,949 A 12/2000 Neuenschwander
6,164,279 A 12/2000 Tweedle
6,171,282 B1 1/2001 Ragsdale
6,183,486 B1 2/2001 Snow et al.
6,197,002 B1 3/2001 Peterson
6,217,555 B1 4/2001 Hart et al.
6,217,590 B1 4/2001 Levinson
6,224,612 B1 5/2001 Bates et al.
6,228,063 B1 5/2001 Aboul-Hosn
6,238,373 B1 5/2001 de la Torre et al.
6,241,768 B1 6/2001 Agarwal et al.
6,254,533 B1 7/2001 Fadem et al.
6,254,534 B1 7/2001 Butler et al.
6,258,065 B1 7/2001 Dennis et al.
6,264,604 B1 7/2001 Kieturakis et al.
6,267,751 B1 7/2001 Mangosong
6,276,661 B1 8/2001 Laird
6,287,280 B1 9/2001 Lampropoulos et al.
6,315,770 B1 11/2001 de la Torre et al.
6,319,246 B1 11/2001 de la Torre et al.
6,322,541 B2 11/2001 West
6,325,384 B1 12/2001 Berry, Sr. et al.
6,346,074 B1 2/2002 Roth
6,355,052 B1 3/2002 Neuss et al.
6,358,266 B1 * 3/2002 Bonutti .............. A61B 17/3439 600/207
6,361,543 B1 * 3/2002 Chin .................. A61B 17/0218 600/207
6,371,968 B1 4/2002 Kogasaka et al.
6,378,944 B1 4/2002 Weisser
6,382,211 B1 5/2002 Crook
6,383,162 B1 5/2002 Sugarbaker
6,391,043 B1 5/2002 Moll et al.
6,413,244 B1 7/2002 Bestetti et al.
6,413,458 B1 7/2002 Pearce
6,420,475 B1 7/2002 Chen
6,423,036 B1 7/2002 Van Huizen
6,440,061 B1 8/2002 Wenner et al.
6,440,063 B1 8/2002 Beane et al.
6,443,957 B1 9/2002 Addis
6,447,489 B1 9/2002 Peterson
6,450,983 B1 9/2002 Rambo
6,454,783 B1 9/2002 Piskun
6,461,332 B1 * 10/2002 Mosel .................... A61B 5/202 600/29
6,464,686 B1 10/2002 O'Hara et al.
6,468,292 B1 10/2002 Mollenauer et al.
6,482,181 B1 11/2002 Racenet et al.
6,482,227 B1 11/2002 Solovay
6,485,435 B1 11/2002 Bakal
6,485,467 B1 11/2002 Crook et al.
6,488,620 B1 12/2002 Segermark et al.
6,488,692 B1 12/2002 Spence et al.
6,494,893 B2 12/2002 Dubrul et al.
6,527,787 B1 3/2003 Fogarty et al.
6,533,734 B1 3/2003 Corley, III et al.
6,551,270 B1 4/2003 Bimbo et al.
6,551,276 B1 4/2003 Mann et al.
6,551,344 B2 4/2003 Thill
6,552,109 B1 4/2003 Chen
6,554,793 B1 4/2003 Pauker et al.
6,558,371 B2 5/2003 Dorn
6,560,782 B2 5/2003 Hourihan et al.
6,569,120 B1 5/2003 Green
6,578,577 B2 6/2003 Bonadio et al.
6,579,281 B2 6/2003 Palmer et al.
6,582,364 B2 6/2003 Butler et al.
6,585,773 B1 7/2003 Xie
6,589,167 B1 7/2003 Shimomura et al.
6,589,211 B1 7/2003 MacLeod
6,607,504 B2 8/2003 Haarala et al.
6,613,952 B2 9/2003 Rambo
6,623,426 B2 9/2003 Bonadio et al.
6,627,275 B1 9/2003 Chen
6,651,670 B2 * 11/2003 Rapacki ............. A61B 17/3468 128/898
6,663,598 B1 12/2003 Carrillo et al.
6,669,674 B1 12/2003 Macoviak et al.
6,676,639 B1 1/2004 Ternström
6,702,787 B2 3/2004 Racenet et al.
6,705,989 B2 3/2004 Cuschieri et al.
6,706,050 B1 3/2004 Giannadakis
6,714,298 B2 3/2004 Ryer
6,716,201 B2 4/2004 Blanco
6,723,044 B2 4/2004 Pulford et al.
6,723,088 B2 4/2004 Gaskill, III et al.
6,725,080 B2 4/2004 Melkent et al.
6,793,621 B2 9/2004 Butler et al.
6,794,440 B2 9/2004 Chen
6,796,940 B2 9/2004 Bonadio et al.
6,797,765 B2 9/2004 Pearce
6,800,084 B2 10/2004 Davison et al.
6,811,546 B1 11/2004 Callas et al.
6,814,078 B2 11/2004 Crook
6,814,700 B1 11/2004 Mueller et al.
6,817,974 B2 11/2004 Cooper et al.
6,830,578 B2 12/2004 O'Heeron et al.
6,837,893 B2 1/2005 Miller
6,840,946 B2 1/2005 Fogarty et al.
6,840,951 B2 1/2005 de la Torre et al.
6,846,287 B2 1/2005 Bonadio et al.

(56) References Cited

U.S. PATENT DOCUMENTS 6,860,463 B2 3/2005 Hartley
6,863,674 B2 3/2005 Kasahara et al.
6,866,861 B1 3/2005 Luhman
6,867,253 B1 3/2005 Chen
6,869,393 B2 3/2005 Butler
6,878,110 B2 4/2005 Yang et al.
6,884,253 B1 4/2005 McFarlane
6,890,295 B2 5/2005 Michels et al.
6,895,965 B2 5/2005 Scarberry et al.
6,901,870 B2 6/2005 Eklof et al.
6,902,541 B2 6/2005 McNally et al.
6,902,569 B2 6/2005 Parmer et al.
6,908,430 B2 6/2005 Caldwell et al.
6,909,220 B2 6/2005 Chen
6,913,609 B2 7/2005 Yencho et al.
6,916,310 B2 7/2005 Sommerich
6,916,331 B2 7/2005 Mollenauer et al.
6,929,637 B2 8/2005 Gonzalez et al.
6,936,005 B2 8/2005 Poff et al.
6,936,037 B2 8/2005 Bubb
6,939,296 B2 9/2005 Ewers et al.
6,945,932 B1 9/2005 Caldwell et al.
6,958,037 B2 10/2005 Ewers et al.
6,958,069 B2 10/2005 Shipp et al.
6,972,026 B1 12/2005 Caldwell et al.
6,979,324 B2 12/2005 Bybordi et al.
6,991,602 B2 1/2006 Nakazawa et al.
6,997,909 B2 2/2006 Goldberg
7,001,397 B2 2/2006 Davison et al.
7,008,377 B2 3/2006 Beane et al.
7,014,628 B2 3/2006 Bousquet
7,033,319 B2 4/2006 Pulford et al.
7,041,056 B2 5/2006 Deslauriers et al.
7,052,454 B2 5/2006 Taylor
7,056,304 B2 6/2006 Bacher et al.
7,056,321 B2 6/2006 Pagliuca et al.
7,067,583 B2 6/2006 Chen
7,077,852 B2 7/2006 Fogarty et al.
7,081,089 B2 7/2006 Bonadio et al.
7,083,626 B2 8/2006 Hart et al.
7,093,599 B2 8/2006 Chen
7,100,614 B2 9/2006 Stevens et al.
7,101,353 B2 9/2006 Liu et al.
7,105,009 B2 9/2006 Johnson
7,105,607 B2 9/2006 Chen
7,112,185 B2 9/2006 Hart et al.
7,118,528 B1 10/2006 Piskun
7,134,929 B2 11/2006 Chen
7,153,261 B2 12/2006 Wenchell
7,163,510 B2 1/2007 Kahle et al.
7,192,436 B2 3/2007 Sing et al.
7,193,002 B2 3/2007 Chen
7,195,590 B2 3/2007 Butler et al.
7,214,185 B1 5/2007 Rosney et al.
7,217,277 B2 5/2007 Parihar et al.
7,222,380 B2 5/2007 Chen
7,223,257 B2 5/2007 Shubayev et al.
7,223,278 B2 5/2007 Davison et al.
7,226,484 B2 6/2007 Chen
7,235,062 B2 6/2007 Brustad
7,235,084 B2 6/2007 Skakoon et al.
7,238,154 B2 7/2007 Ewers et al.
7,244,244 B2 7/2007 Racenet et al.
7,276,075 B1 10/2007 Callas et al.
7,290,367 B2 11/2007 Chen
7,294,103 B2 * 11/2007 Bertolero .............. A61B 17/02 600/201
7,297,106 B2 11/2007 Yamada et al.
7,300,399 B2 11/2007 Bonadio et al.
7,311,661 B2 * 12/2007 Heinrich ........... A61B 17/0218 600/206
7,316,699 B2 1/2008 McFarlane
7,331,940 B2 2/2008 Sommerich
7,338,473 B2 3/2008 Campbell et al.
7,344,547 B2 3/2008 Piskun
7,344,568 B2 3/2008 Chen
7,377,898 B2 5/2008 Ewers et al.
7,390,317 B2 6/2008 Taylor et al.
7,393,322 B2 7/2008 Wenchell
7,412,977 B2 8/2008 Fields et al.
7,445,597 B2 11/2008 Butler et al.
7,445,598 B2 * 11/2008 Orban, III .......... A61B 17/0218 600/210
7,473,221 B2 1/2009 Ewers et al.
7,481,765 B2 1/2009 Ewers et al.
7,537,564 B2 5/2009 Bonadio et al.
7,540,839 B2 6/2009 Butler et al.
7,559,893 B2 7/2009 Bonadio et al.
7,578,832 B2 8/2009 Johnson
7,645,232 B2 1/2010 Shluzas
7,650,887 B2 1/2010 Nguyen et al.
7,661,164 B2 2/2010 Chen
7,704,207 B2 4/2010 Albrecht et al.
7,717,847 B2 5/2010 Smith
7,727,146 B2 6/2010 Albrecht et al.
7,727,255 B2 6/2010 Taylor et al.
7,736,306 B2 6/2010 Brustad et al.
7,749,415 B2 7/2010 Brustad et al.
7,753,901 B2 7/2010 Piskun et al.
7,758,500 B2 7/2010 Boyd et al.
7,766,823 B2 * 8/2010 Moll .................. A61B 17/0218 600/192
7,766,824 B2 8/2010 Jensen et al.
7,811,251 B2 10/2010 Wenchell et al.
7,815,567 B2 10/2010 Albrecht et al.
7,837,612 B2 11/2010 Gill et al.
7,841,765 B2 11/2010 Keller
7,850,667 B2 12/2010 Gresham
7,867,164 B2 1/2011 Butler et al.
7,878,974 B2 2/2011 Brustad et al.
7,896,889 B2 3/2011 Mazzocchi et al.
7,909,760 B2 3/2011 Albrecht et al.
7,930,782 B2 4/2011 Chen
8,033,995 B2 * 10/2011 Cropper ............. A61B 17/3423 600/207
8,641,758 B1 * 2/2014 Anderson .......... A61B 17/0206 623/23.64
2001/0037053 A1 11/2001 Bonadio et al.
2001/0047188 A1 11/2001 Bonadio et al.
2002/0002324 A1 1/2002 McManus
2002/0010389 A1 1/2002 Butler et al.
2002/0013542 A1 1/2002 Bonadio et al.
2002/0016607 A1 2/2002 Bonadio et al.
2002/0026230 A1 2/2002 Moll et al.
2002/0038077 A1 3/2002 de la Torre et al.
2002/0072762 A1 * 6/2002 Bonadio ............ A61B 17/3423 606/192
2002/0111536 A1 8/2002 Cuschieri et al.
2002/0156432 A1 10/2002 Racenet
2002/0162559 A1 11/2002 Crook
2002/0014076 A1 1/2003 Mollenauer
2003/0004253 A1 1/2003 Chen
2003/0028179 A1 2/2003 Piskun
2003/0040711 A1 2/2003 Racenet et al.
2003/0059865 A1 3/2003 Nelson
2003/0078476 A1 4/2003 Hill
2003/0078478 A1 4/2003 Bonadio et al.
2003/0139756 A1 7/2003 Brustad
2003/0167040 A1 9/2003 Bacher et al.
2003/0187376 A1 10/2003 Rambo
2003/0191371 A1 10/2003 Smith et al.
2003/0192553 A1 10/2003 Rambo
2003/0225392 A1 12/2003 McMichael et al.
2003/0236505 A1 12/2003 Bonadio et al.
2003/0236549 A1 12/2003 Bonadio et al.
2004/0015185 A1 1/2004 Ewers et al.
2004/0024363 A1 2/2004 Goldberg
2004/0049099 A1 3/2004 Ewers et al.
2004/0049100 A1 3/2004 Butler
2004/0054353 A1 3/2004 Taylor
2004/0106942 A1 3/2004 Taylor
2004/0063833 A1 4/2004 Chen
2004/0068232 A1 4/2004 Hart et al.
2004/0070187 A1 4/2004 Chen

(56) References Cited

U.S. PATENT DOCUMENTS

2004/0072942 A1 4/2004 Chen
2004/0073090 A1 4/2004 Butler
2004/0092795 A1 5/2004 Bonadio et al.
2004/0092796 A1 5/2004 Butler et al.
2004/0093018 A1 5/2004 Johnson
2004/0097793 A1 5/2004 Butler et al.
2004/0111061 A1 6/2004 Curran
2004/0127772 A1 7/2004 Ewers et al.
2004/0138529 A1 7/2004 Wiltshire et al.
2004/0143158 A1 7/2004 Hart et al.
2004/0154624 A1 8/2004 Bonadio et al.
2004/0167559 A1 8/2004 Taylor et al.
2004/0173218 A1 9/2004 Yamada et al.
2004/0215063 A1 10/2004 Bonadio et al.
2004/0230161 A1 11/2004 Zeiner
2004/0243144 A1 12/2004 Bonadio et al.
2004/0249248 A1 12/2004 Bonadio et al.
2004/0254426 A1 12/2004 Wenchell
2004/0260244 A1 12/2004 Piechowicz et al.
2004/0267096 A1 12/2004 Caldwell et al.
2005/0020884 A1 1/2005 Hart et al.
2005/0033246 A1 2/2005 Ahlbert et al.
2005/0033327 A1 2/2005 Gainor et al.
2005/0059865 A1 3/2005 Kahle et al.
2005/0065475 A1 3/2005 Hart et al.
2005/0065543 A1 3/2005 Kahle et al.
2005/0080319 A1 4/2005 Dinkier, II et al.
2005/0090713 A1 4/2005 Gozales et al.
2005/0090716 A1 4/2005 Bonadio et al.
2005/0090717 A1 4/2005 Bonadio et al.
2005/0096695 A1 5/2005 Olich
2005/0131349 A1 6/2005 Albrecht et al.
2005/0148823 A1 7/2005 Vaugh et al.
2005/0155611 A1 7/2005 Vaugh et al.
2005/0159647 A1 7/2005 Hart et al.
2005/0159650 A1 7/2005 Raymond et al.
2005/0165281 A1 7/2005 Ravikumar et al.
2005/0192483 A1 9/2005 Bonadio et al.
2005/0192598 A1 9/2005 Johnson et al.
2005/0197537 A1 9/2005 Bonadio et al.
2005/0203346 A1 9/2005 Bonadio et al.
2005/0209510 A1 9/2005 Bonadio et al.
2005/0215863 A1 9/2005 Ravikumar et al.
2005/0222582 A1 10/2005 Wenchell
2005/0228447 A1 10/2005 Rambo
2005/0240082 A1 10/2005 Bonadio et al.
2005/0241647 A1 11/2005 Nguyen
2005/0251124 A1 11/2005 Zvuloni et al.
2005/0261720 A1 11/2005 Caldwell et al.
2005/0267419 A1 12/2005 Smith
2005/0277946 A1 12/2005 Greenhalgh
2005/0283050 A1 12/2005 Gundlapalli et al.
2005/0288558 A1 12/2005 Ewers et al.
2005/0288634 A1 12/2005 O'Heeron et al.
2006/0019137 A1 1/2006 Fukuda
2006/0020164 A1 1/2006 Butler et al.
2006/0020241 A1 1/2006 Piskun et al.
2006/0030755 A1 2/2006 Ewers et al.
2006/0041270 A1 2/2006 Lenker
2006/0047284 A1 3/2006 Gresham
2006/0047293 A1 3/2006 Haberland et al.
2006/0052669 A1 3/2006 Hart
2006/0084842 A1 4/2006 Hart et al.
2006/0106402 A1 5/2006 McLucas
2006/0129165 A1 6/2006 Edoga et al.
2006/0149137 A1 7/2006 Pingleton et al.
2006/0149306 A1 7/2006 Hart et al.
2006/0161049 A1 7/2006 Beane et al.
2006/0161050 A1 7/2006 Butler et al.
2006/0241651 A1 10/2006 Wilk
2006/0247498 A1 11/2006 Bonadio et al.
2006/0247499 A1 11/2006 Butler et al.
2006/0247500 A1 11/2006 Voegele et al.
2006/0247516 A1 11/2006 Hess et al.
2006/0247586 A1 11/2006 Voegele et al.
2006/0247673 A1 11/2006 Voegele et al.
2006/0247678 A1 11/2006 Weisenburgh, II et al.
2006/0258899 A1 11/2006 Gill et al.
2006/0264706 A1 11/2006 Piskun
2006/0270911 A1 11/2006 Voegele et al.
2007/0004968 A1 1/2007 Bonadio et al.
2007/0049966 A1 3/2007 Bonadio et al.
2007/0088202 A1 4/2007 Albrecht et al.
2007/0088204 A1* 4/2007 Albrecht ................ A61B 17/02 600/208
2007/0093695 A1 4/2007 Bonadio et al.
2007/0118175 A1 5/2007 Butler et al.
2007/0142780 A1 6/2007 Van Lue
2007/0149859 A1 6/2007 Albrecht et al.
2007/0151566 A1 7/2007 Kahle et al.
2007/0156023 A1 7/2007 Frasier et al.
2007/0156024 A1 7/2007 Frasier et al.
2007/0185387 A1 8/2007 Albrecht et al.
2007/0203398 A1 8/2007 Bonadio et al.
2007/0208312 A1 9/2007 Norton et al.
2007/0255219 A1 11/2007 Vaugh et al.
2007/0270654 A1 11/2007 Pignato et al.
2007/0270752 A1 11/2007 LaBombard
2007/0299387 A1 12/2007 Williams et al.
2008/0027476 A1 1/2008 Piskun
2008/0048011 A1 2/2008 Weller
2008/0097162 A1 4/2008 Bonadio et al.
2008/0097163 A1 4/2008 Butler et al.
2008/0103366 A1 5/2008 Banchieri et al.
2008/0200767 A1 8/2008 Ewers et al.
2008/0255519 A1 10/2008 Piskun et al.
2008/0281161 A1 11/2008 Albrecht et al.
2008/0281162 A1 11/2008 Albrecht et al.
2009/0012477 A1 1/2009 Norton et al.
2009/0036745 A1 2/2009 Bonadio et al.
2009/0069627 A1 3/2009 Haindl
2009/0069837 A1 3/2009 Bonadio et al.
2009/0093683 A1 4/2009 Richard et al.
2009/0093752 A1 4/2009 Richard et al.
2009/0131754 A1 5/2009 Ewers et al.
2009/0137879 A1 5/2009 Ewers et al.
2009/0149714 A1 6/2009 Bonadio
2009/0182279 A1 7/2009 Wenchell et al.
2009/0182282 A1 7/2009 Okihisa et al.
2009/0187079 A1 7/2009 Albrecht et al.
2009/0227843 A1 9/2009 Smith et al.
2009/0292176 A1 11/2009 Bonadio et al.
2009/0326330 A1 12/2009 Bonadio et al.
2010/0063362 A1 3/2010 Bonadio et al.
2010/0063364 A1 3/2010 Bonadio et al.
2010/0063452 A1 3/2010 Edelman et al.
2010/0081880 A1 4/2010 Widenhouse et al.
2010/0081881 A1 4/2010 Murray et al.
2010/0081995 A1 4/2010 Widenhouse et al.
2010/0094227 A1 4/2010 Albrecht et al.
2010/0100043 A1 4/2010 Racenet
2010/0113882 A1 5/2010 Widenhouse et al.
2010/0217087 A1 8/2010 Bonadio et al.
2010/0228091 A1 9/2010 Widenhouse et al.
2010/0228092 A1 9/2010 Ortiz et al.
2010/0228094 A1 9/2010 Ortiz et al.
2010/0240960 A1 9/2010 Richard
2010/0249523 A1 9/2010 Spiegel et al.
2010/0249524 A1 9/2010 Ransden et al.
2010/0249525 A1 9/2010 Shelton, IV et al.
2010/0249694 A1 9/2010 Choi et al.
2010/0261972 A1 10/2010 Widenhouse et al.
2010/0261975 A1 10/2010 Huey et al.
2010/0286484 A1 11/2010 Stellon et al.
2010/0298646 A1 11/2010 Stellon et al.
2010/0305407 A1 12/2010 Farley
2011/0021877 A1 1/2011 Fortier et al.
2011/0028891 A1 2/2011 Okoniewski
2011/0034935 A1 2/2011 Kleyman
2011/0034946 A1 2/2011 Kleyman
2011/0034947 A1 2/2011 Kleyman
2011/0054260 A1 3/2011 Albrecht et al.
2011/0071462 A1 3/2011 Ewers et al.
2011/0071463 A1 3/2011 Ewers et al.

(56) References Cited

U.S. PATENT DOCUMENTS

| | | | |
|---|---|---|---|
| 2011/0144443 | A1 | 6/2011 | Shelton, IV et al. |
| 2011/0160820 | A1 | 6/2011 | Jackson et al. |
| 2012/0095297 | A1 | 4/2012 | Dang et al. |
| 2013/0072759 | A1 | 3/2013 | Li et al. |
| 2013/0245381 | A1 | 9/2013 | Dang et al. |
| 2013/0296655 | A1 | 11/2013 | Hart et al. |
| 2015/0164552 | A1 | 6/2015 | Chen et al. |

FOREIGN PATENT DOCUMENTS

| | | | |
|---|---|---|---|
| DE | 33 36 279 | C2 | 1/1986 |
| DE | 37 39 532 | C1 | 12/1988 |
| DE | 37 37 121 | A1 | 5/1989 |
| DE | 296 00 939 | U1 | 6/1996 |
| DE | 19828009 | A1 | 12/1999 |
| EP | 0 113 520 | A2 | 7/1984 |
| EP | 0 142 262 | A1 | 5/1985 |
| EP | 0 517 248 | A1 | 12/1992 |
| EP | 0 537 768 | A1 | 4/1993 |
| EP | 0 807 416 | A2 | 11/1997 |
| EP | 0 849 517 | B1 | 6/1998 |
| EP | 0 950 376 | B1 | 10/1999 |
| EP | 1 118 657 | A1 | 7/2001 |
| EP | 1 125 552 | A1 | 8/2001 |
| EP | 1 312 318 | B1 | 5/2003 |
| EP | 1 407 715 | A1 | 4/2004 |
| EP | 1 609 429 | A2 | 12/2005 |
| EP | 1 609 429 | A3 | 12/2005 |
| EP | 2 044 889 | A1 | 4/2009 |
| EP | 2 260 777 | A1 | 12/2010 |
| EP | 2 272 450 | A3 | 1/2011 |
| EP | 2 340 792 | A1 | 7/2011 |
| EP | 2 486 882 | A2 | 8/2012 |
| EP | 2 589 443 | A1 | 5/2013 |
| EP | 2 609 880 | A1 | 7/2013 |
| EP | 2 617 373 | A1 | 7/2013 |
| FR | 1 456 623 | | 9/1966 |
| GB | 1 151 993 | | 5/1969 |
| GB | 1 355 611 | | 6/1974 |
| GB | 1 372 491 | | 10/1974 |
| GB | 1 379 772 | | 1/1975 |
| GB | 1 400 808 | | 7/1975 |
| GB | 1 407 023 | | 9/1975 |
| GB | 1 482 857 | | 8/1977 |
| GB | 1 496 696 | | 12/1977 |
| GB | 2 071 502 | | 9/1981 |
| GB | 2 255 019 | | 10/1992 |
| GB | 2 275 420 | | 8/1994 |
| GB | 2 298 906 | | 9/1996 |
| IE | 930649 | | 9/1993 |
| IE | 930650 | | 9/1993 |
| IE | S940150 | | 2/1994 |
| IE | S940613 | | 8/1994 |
| IE | S940960 | | 12/1994 |
| IE | S950055 | | 1/1995 |
| IE | S950266 | | 4/1995 |
| IE | S71634 | | 2/1997 |
| IE | S75368 | | 8/1997 |
| IE | S960196 | | 8/1997 |
| IE | S970810 | | 11/1997 |
| IE | 991010 | | 7/2000 |
| IE | 990218 | | 11/2000 |
| IE | 990219 | | 11/2000 |
| IE | 990220 | | 11/2000 |
| IE | 990660 | | 2/2001 |
| IE | 990795 | | 3/2001 |
| JP | 10-108868 | A | 4/1998 |
| JP | 11-290327 | A | 10/1999 |
| JP | 2001-61850 | A | 3/2001 |
| JP | 2002-28163 | A | 1/2002 |
| JP | 2003-235879 | A | 8/2003 |
| JP | 2004-195037 | A | 7/2004 |
| JP | 2007-44395 | A | 2/2007 |
| KR | 20140074622 | A | 6/2014 |
| SU | 1342485 | A1 | 1/1997 |
| WO | WO 86/06272 | A1 | 11/1986 |
| WO | WO 86/06316 | A1 | 11/1986 |
| WO | WO 92/11880 | A1 | 7/1992 |
| WO | WO 92/21292 | A2 | 12/1992 |
| WO | WO 93/05740 | A1 | 4/1993 |
| WO | WO 93/14801 | A1 | 8/1993 |
| WO | WO 94/04067 | A1 | 3/1994 |
| WO | WO 94/22357 | A2 | 10/1994 |
| WO | WO 95/05207 | A2 | 2/1995 |
| WO | WO 95/07056 | A2 | 3/1995 |
| WO | WO 95/22289 | A2 | 8/1995 |
| WO | WO 95/24864 | A1 | 9/1995 |
| WO | WO 95/27445 | A1 | 10/1995 |
| WO | WO 95/27468 | A1 | 10/1995 |
| WO | WO 96/36283 | A1 | 11/1996 |
| WO | WO 97/11642 | A1 | 4/1997 |
| WO | WO 97/32514 | A2 | 9/1997 |
| WO | WO 97/32515 | A1 | 9/1997 |
| WO | WO 97/42889 | A1 | 11/1997 |
| WO | WO 98/19853 | A1 | 5/1998 |
| WO | WO 98/35614 | A1 | 8/1998 |
| WO | WO 98/48724 | A1 | 11/1998 |
| WO | WO 99/03416 | A1 | 1/1999 |
| WO | WO 99/15068 | A2 | 4/1999 |
| WO | WO 99/16368 | A1 | 4/1999 |
| WO | WO 99/22804 | A1 | 5/1999 |
| WO | WO 99/25268 | A1 | 5/1999 |
| WO | WO 99/29250 | A1 | 6/1999 |
| WO | WO 00/32116 | A1 | 6/2000 |
| WO | WO 00/32117 | A1 | 6/2000 |
| WO | WO 00/32119 | A1 | 6/2000 |
| WO | WO 00/32120 | A1 | 6/2000 |
| WO | WO 00/35356 | A1 | 6/2000 |
| WO | WO 00/47117 | A1 | 8/2000 |
| WO | WO 00/54675 | A1 | 9/2000 |
| WO | WO 00/54676 | A1 | 9/2000 |
| WO | WO 00/54677 | A1 | 9/2000 |
| WO | WO 01/08563 | A2 | 2/2001 |
| WO | WO 01/08581 | A2 | 2/2001 |
| WO | WO 01/26558 | A1 | 4/2001 |
| WO | WO 01/26559 | A1 | 4/2001 |
| WO | WO 01/045568 | A1 | 6/2001 |
| WO | WO 01/49363 | A1 | 7/2001 |
| WO | WO 01/91652 | A1 | 12/2001 |
| WO | WO 02/07611 | A2 | 1/2002 |
| WO | WO 02/17800 | A2 | 3/2002 |
| WO | WO 02/34108 | A2 | 5/2002 |
| WO | WO 03/011153 | A1 | 2/2003 |
| WO | WO 03/011551 | A1 | 2/2003 |
| WO | WO 03/026512 | A1 | 4/2003 |
| WO | WO 03/032819 | A1 | 4/2003 |
| WO | WO 03/034908 | A2 | 5/2003 |
| WO | WO 03/034908 | A3 | 5/2003 |
| WO | WO 03/061480 | A1 | 7/2003 |
| WO | WO 03/077726 | A2 | 9/2003 |
| WO | WO 03/103548 | A1 | 12/2003 |
| WO | WO 2004/026153 | A1 | 4/2004 |
| WO | WO 2004/030547 | A1 | 4/2004 |
| WO | WO 2004/075730 | A2 | 9/2004 |
| WO | WO 2004/075741 | A2 | 9/2004 |
| WO | WO 2004/075930 | A2 | 9/2004 |
| WO | WO 2005/009257 | A2 | 2/2005 |
| WO | WO 2005/034766 | A2 | 4/2005 |
| WO | WO 2005/089661 | A1 | 9/2005 |
| WO | WO 2006/057982 | A2 | 1/2006 |
| WO | WO 2006/040748 | A1 | 4/2006 |
| WO | WO 2006/059318 | A1 | 6/2006 |
| WO | WO 2006/100658 | A2 | 9/2006 |
| WO | WO 2007/044849 | A1 | 4/2007 |
| WO | WO 2008/011358 | A1 | 1/2008 |
| WO | WO 2008/015566 | A2 | 2/2008 |
| WO | WO 2008/045935 | A2 | 4/2008 |
| WO | WO 2008/093313 | A1 | 8/2008 |
| WO | WO 2008/121294 | A1 | 10/2008 |
| WO | WO 2009/117435 | A2 | 9/2009 |
| WO | WO 2010/045253 | A1 | 4/2010 |
| WO | WO 2010/082722 | A1 | 7/2010 |
| WO | WO 2010/104259 | A1 | 9/2010 |
| WO | WO 2010/141673 | A1 | 12/2010 |

(56) References Cited

FOREIGN PATENT DOCUMENTS

| | | |
|---|---|---|
| WO | WO 2012/154845 A1 | 11/2012 |
| WO | WO 2013/106569 A2 | 7/2013 |
| WO | WO 2014/174031 A1 | 10/2014 |

OTHER PUBLICATIONS

European Patent Office, The International Search Report and Written Opinion for International Application No. PCT/US2011/054266, titled "Natural Orifice Surgery System," dated Feb. 9, 2012, 13 pages.

European Patent Office, The International Search Report and Written Opinion for International Application No. PCT/US2012/037111, "Wound Retractor," dated Aug. 30, 2012, 21 pgs.

The International Bureau of WIPO, International Preliminary Report on Patentability for International Application No. PCT/US2011/054266, titled "Natural Orifice Surgery System", dated Apr. 2, 2013, 8 pgs.

European Patent Office, The International Written Opinion for International Application No. PCT/US2013/037213, titled "Natural Orifice Surgery System," dated Jul. 3, 2013, 6 pgs.

The International Bureau of WIPO, International Preliminary Report on Patentability for International Application No. PCT/US2013/037213, titled "Natural Orifice Surgery System," dated Oct. 21, 2014, 8 pgs.

European Patent Office, The International Search Report and Written Opinion for International Application No. PCT/US2012/060997, titled "Simulated Tissue Structure for Surgical Training," dated Mar. 7, 2013 8 pgs.

European Patent Office, The International Search Report and Written Opinion for International Application No. PCT/US2015/045201, titled "Natural Orifice Surgery System," dated Sep. 25, 2015, 11 pgs.

European Patent Office, The International Search Report for International Application No. PCT/US2013/0037213, titled "Natural Orifice Surgery System," dated Jul. 3, 2013, 3 pgs.

The International Bureau of WIPO, International Preliminary Report on Patentability for International Application No. PCT/US2015/045201, titled "Natural Orifice Surgery System", dated Mar. 2, 2017, 9 pgs.

European Patent Office, The International Search Report and Written Opinion of the International Searching Authority for International Application No. PCT/US2016/049079, titled "Wound Retractors with Non-Circular, Non-Coplanar or Non-Parallel Inner Rings," dated Apr. 5, 2017, 21 pgs.

The International Searching Authority, The International Search Report and Written Opinion of the International Searching Authority for International Application No. PCT/US2015/062326, dated Jun. 21, 2016, 22 pgs.

U.S. Appl. No. 10/381,220, filed Mar. 20, 2003; Title: Surgical Access Apparatus and Method, now U.S. Pat. No. 7,473,221 issued Jan. 6, 2009.

U.S. Appl. No. 10/436,522, filed May 13, 2003; Title: Laparoscopic Illumination Apparatus and Method, now U.S. Pat. No. 6,939,296 issued Sep. 6, 2005.

U.S. Appl. No. 10/399,209, filed Aug. 22, 2003; Title: Wound Retraction Apparatus and Method, now U.S. Pat. No. 6,958,037 issued Oct. 25, 2005.

U.S. Appl. No. 11/218,412, filed Sep. 1, 2005; Title: Wound Retraction Apparatus and Method, now U.S. Pat. No. 7,238,154 issued Jul. 3, 2007.

U.S. Appl. No. 10/399,057, filed Apr. 11, 2003; Title: Sealed Surgical Access Device, now U.S. Pat. No. 7,052,454 issued May 30, 2006.

U.S. Appl. No. 10/666,579, filed Sep. 17, 2003; Title: Surgical Instrument Access Device, now U.S. Pat. No. 7,163,510 issued Jan. 16, 2007.

U.S. Appl. No. 10/052,297, filed Jan. 18, 2002; Title: Hand Access Port Device, now U.S. Pat. No. 6,908,430 issued Jun. 21, 2005.

U.S. Appl. No. 08/015,765, filed Feb. 10, 1993; Title: Gas-Tight Seal Accomodating Surgical Instruments With a Wide Range of Diameters, now U.S. Pat. No. 5,407,433 issued Apr. 18, 1995.

U.S. Appl. No. 08/040,373, filed Mar. 30, 1993; Title: Gas-Tight Seal Accomodating Surgical Instruments With a Wide Range of Diameters, now U.S. Pat. No. 5,411,483 issued May 2, 1995.

U.S. Appl. No. 10/902,756, filed Jul. 29, 2004; Title: Hand Access Port Device, now abandoned.

U.S. Appl. No. 10/802,125, filed Mar. 15, 2004; Title: Surgical Guide Valve, now abandoned.

U.S. Appl. No. 10/516,198, filed Nov. 30, 2004; Title: Wound Retractor, now U.S. Appl. No. 7,650,887 issued Jan. 26, 2010.

U.S. Appl. No. 10/927,551, filed Aug. 25, 2004; Title: Surgical Access System, now abandoned.

U.S. Appl. No. 11/244,647, filed Oct. 5, 2005; Title: Surgical Access Apparatus and Method, now U.S. Pat. No. 7,481,765 issued Jan. 27, 2009.

U.S. Appl. No. 11/548,746, filed Oct. 12, 2006; Title: Method of Making a Hand Access Laparoscopic Device, now U.S. Appl. No. 7,749,415 issued Jul. 6, 2010.

U.S. Appl. No. 11/548,765, filed Oct. 12, 2006; Title: Split Hoop Wound Retractor, now U.S. Appl. No. 7,815,567 issued Oct. 26, 2010.

U.S. Appl. No. 11/548,767, filed Oct. 12, 2006; Title: Circular Surgical Retractor now U.S. Appl. No. 7,704,207 issued Apr. 27, 2010.

U.S. Appl. No. 11/548,781, filed Oct. 12, 2006; Title: Wound Retractor With Gel Cap, now U.S. Appl. No. 7,727,146 issued Jun. 1, 2010.

U.S. Appl. No. 11/548,955, filed Oct. 12, 2006; Title: Hand Access Laparoscopic Device, now U.S. Pat. No. 7,736,306 issued Jun. 15, 2010.

U.S. Appl. No. 11/755,305, filed May 30, 2007; Title: Wound Retraction Apparatus and Method, now U.S. Pat. No. 7,377,898 issued May 27, 2008.

U.S. Appl. No. 11/548,758, filed Oct. 12, 2006; Title: Split Hoop Wound Retractor With Gel Pad, now U.S. Pat. No. 7,909,760 issued Mar. 22, 2011.

U.S. Appl. No. 12/693,242, filed Jan. 1, 2010; Title: Wound Retractor, now U.S. Pat. No. 7,913,697 issued Mar. 29, 2011.

U.S. Appl. No. 12/768,328, filed Apr. 27, 2010; Title: Circular Surgical Retractor, now U.S. Pat. No. 7,892,172 issued Feb. 22, 2011.

U.S. Appl. No. 12/791,666, filed Jun. 1, 2010; Title: Wound Retractor With Gel CAP, now U.S. Pat. No. 7,883,461 issued Feb. 8, 2011.

U.S. Appl. No. 12/815,986, filed Jun. 15, 2010; Title: Hand Access Laparoscopic Device, now U.S. Pat. No. 7,878,974 issued Feb. 1, 2011.

U.S. Appl. No. 10/695,295, filed Oct. 28, 2003; Title: Surgical Gel Seal.

U.S. Appl. No. 11/132,741, filed May 18, 2005; Title: Gas-Tight Seal Accomodating Surgical Instruments With a Wide Range of Diameters.

U.S. Appl. No. 11/245,709, filed Oct. 7, 2005; Title: Surgical Access System.

U.S. Appl. No. 11/330,661, filed Jan. 12, 2006; Title: Sealed Surgical Access Device.

U.S. Appl. No. 11/564,409, filed Nov. 29, 2006; Title: Surgical Instrument Access Device.

U.S. Appl. No. 12/108,400, filed Apr. 23, 2008; Title: Wound Retraction Apparatus and Method.

U.S. Appl. No. 12/119,371, filed May 12, 2008; Title: Surgical Retractor With Gel Pad.

U.S. Appl. No. 12/119,414, filed May 12, 2008; Title: Surgical Retractor.

U.S. Appl. No. 12/358,080, filed Jan. 22, 2009; Title: Surgical Instrument Access Device.

U.S. Appl. No. 12/360,634, filed Jan. 27, 2009; Title: Surgical Access Apparatus and Method.

U.S. Appl. No. 12/360,710, filed Jan. 27, 2009; Title: Surgical Access Apparatus and Method.

(56) References Cited

OTHER PUBLICATIONS

U.S. Appl. No. 12/578,422, filed Oct. 13, 2009; Title: Single Port Access System.
U.S. Appl. No. 12/905,932, filed Oct. 15, 2010; Title: Split Hoop Wound Retractor.
U.S. Appl. No. 12/960,449, filed Dec. 3, 2010; Title: Surgical Access Apparatus and Method.
U.S. Appl. No. 12/960,458, filed Dec. 3, 2010; Title: Surgical Access Apparatus and Method.
U.S. Appl. No. 13/006,727, filed Jan. 14, 2011.
U.S. Appl. No. 13/008,728, filed Jan. 18, 2011.
U.S. Appl. No. 13/023,334, filed Feb. 8, 2011.
U.S. Appl. No. 13/031,892, filed Feb. 22, 2011.
U.S. Appl. No. 13/050,042, filed Mar. 17, 2011.
U.S. Appl. No. 10/446,365, filed May 28, 2003; Title: Screw-Type Seal With Inflatable Membrane.
U.S. Appl. No. 12/004,439, filed Dec. 20, 2007; Title: Skin Seal.
U.S. Appl. No. 12/004,441, filed Dec. 20, 2007; Title: Screw-Type Skin Seal With Inflatable Membrane.
U.S. Appl. No. 12/607,667, filed Oct. 28, 2009; Title: Screw-Type Skin Seal With Inflatable Membrane.
U.S. Appl. No. 10/965,217, filed Oct. 15, 2004; Title: Surgical Sealing Device.
U.S. Appl. No. 10/981,730, filed Nov. 5, 2004; Title: Surgical Sealing Device.
U.S. Appl. No. 11/246,909, filed Oct. 11, 2005; Title: Instrument Access Device.
U.S. Appl. No. 11/291,089, filed Dec. 1, 2005; Title: A Surgical Sealing Device.
U.S. Appl. No. 11/486,383, filed Jul. 14, 2006; Title: Wound Retractor.
U.S. Appl. No. 11/785,752, filed Apr. 19, 2007; Title: Instrument Access Device.
U.S. Appl. No. 12/244,024, filed Oct. 2, 2008; Title: Seal Anchor for Use in Surgical Procedures.
U.S. Appl. No. 12/578,832, filed Oct. 14, 2009; Title: Flexible Access Device for Use in Surgical Procedure.
U.S. Appl. No. 12/706,043, filed Feb. 16, 2010; Title: Flexible Port Seal.
U.S. Appl. No. 12/719,341, filed Mar. 8, 2010; Title: Foam Port and Introducer Assembly.
U.S. Appl. No. 10/895,546, filed Jul. 21, 2004; Title: Laparoscopic Instrument and Cannula Assembly and Related Surgical Method.
U.S. Appl. No. 10/913,565, filed Aug. 5, 2004; Title: Surgical Device With Tack-Free Gel and Method of Manufacture.
Declaration of John R. Brustad dated Dec. 10, 2009, submitted in U.S. Appl. No. 11/548,955, including Appendices A-D regarding product sales brochures and production drawings from 2001 and 2005.
Dexterity Protractor Instruction Manual by Dexterity Surgical, Inc.
European Patent Office, European Search Report for European Application No. EP 10 18 4681, dated Nov. 22, 2010, entitled "Wound Retraction Apparatus and Method".
European Patent Office, European Search Report for European Application No. EP 10 18 4608, dated Nov. 22, 2010, entitled "Wound Retraction Apparatus and Method".
European Patent Office, European Search Report for European Application No. EP 10 18 4648, dated Nov. 22, 2010, entitled "Wound Retraction Apparatus and Method".
European Patent Office, European Search Report for European Application No. EP 10 18 4731, dated Nov. 22, 2010, entitled "Wound Retraction Apparatus and Method".
European Patent Office, European Search Report for European Application No. EP 10 18 4661, dated Nov. 22, 2010, entitled "Wound Retraction Apparatus and Method".
European Patent Office, European Search Report for European Application No. EP 10 18 4677, dated Nov. 22, 2010, entitled "Wound Retraction Apparatus and Method".
European Patent Office, European Search Report for European Application No. EP 10 18 9325, dated Dec. 14, 2010, entitled "Split Hoop Wound Retractor".
European Patent Office, European Search Report for European Application No. EP 10 18 9328, dated Dec. 15, 2010, entitled "Split Hoop Wound Retractor".
European Patent Office, European Search Report for European Application No. EP 04 00 2888, dated Sep. 10, 2004, entitled "Hand Access Port Device".
European Patent Office, European Search Report for European Application No. EP 04 00 2889, dated Sep. 13, 2004, entitled "Hand Access Port Device".
European Patent Office, International Search Report and the Written Opinion of the International Searching Authority for International Application No. PCT/US2006/040154, dated Jan. 30, 2007.
European Patent Office, International Search Report and the Written Opinion of the International Searching Authority for International Application No. PCT/US2006/040073, dated Jan. 26, 2007.
European Patent Office, International Search Report and the Written Opinion of the International Searching Authority for International Application No. PCT/US2006/039905, dated Jan. 17, 2007.
European Patent Office, International Search Report and the Written Opinion of the International Searching Authority for International Application No. PCT/US2006/039883, dated Jan. 31, 2007.
European Patent Office, International Search Report and the Written Opinion of the International Searching Authority for International Application No. PCT/US2006/039800, dated Apr. 16, 2007.
European Patent Office, International Search Report and the Written Opinion of the International Searching Authority for International Application No. PCT/US2006/039799, dated Mar. 27, 2007.
European Patent Office, European Search Report for European Patent No. 11172709.5, dated Aug. 16, 2011.
European Patent Office, European Search Report for European Patent No. 11172706.1, dated Aug. 16, 2011.
European Patent Office, European Search Report for European Application No. 15173370.6, dated Aug. 7, 2015, entitled "Wound Retractor," (3 pgs.).
European Search Report for corresponding EP 08253236 dated Feb. 10, 2009 (6 pages).
Harold W. Harrower, M.D. Isolation of Incisions into Body Cavities, The American Journal of Surgery, p. 824-826.
Horigame, et al., Silicone Rumen Cannula with a Soft Cylindrical Part and a Hard Flange, Journal of Dairy Science, Nov. 1989, vol. 72, No. 11, pp. 3230-3232.
Horigame, et al., Technical Note: Development of Duodoenal Cannula for Sheep, Journal of Animal Science, Apr. 1992, vol. 70, Issue 4, pp. 1216-1219.
International Searching Authority/US, International Search Report and the Written Opinion of the International Searching Authority for International Application No. PCT/USO4/05484.
International Searching Authority/US, International Search Report and the Written Opinion of the International Searching Authority for International Application No. PCT/US01/29682.
Kagaya, Laparascopic cholecystecomy via two ports, using the "Twin-Port" system, J. Hepatobiliary Pancreat Surg (2001) 8:76-80.
McSweeney, Cannulation of the Rumen in Cattle and Buffaloes, Australian Veterniary Journal, Aug. 1989, vol. 66, No. 8, pp. 266-268.
Neil Sheehan, Supplemental Expert Report of Neil Sheehan, Re: U.S. Pat. No. 5,741,298, United States District Court for the Central District of California, Civil Action No. SACV 03-1322 JVS, Aug. 9, 2005.
Office Action in co-pending patent U.S. Appl. No. 12/360,634, dated Jan. 24, 2011 in 12 pages.
Office Action in co-pending patent U.S. Appl. No. 12/360,710, dated Jan. 24, 2011 in 12 pages.
Technical Note: Development of Duodenal Cannula for Sheep, Faculty of Agriculture and School of Medicine Tohokju University, Sendai 981, Japan.
The International Bureau of WIPO, International Preliminary Report on Patentability, dated Aug. 29, 2006, for International Application No. PCT/US2004/028250.

(56) References Cited

OTHER PUBLICATIONS

The International Bureau of WIPO, International Preliminary Report on Patentability, dated Apr. 16, 2008, for International Application No. PCT/US2006/039799.

The International Bureau of WIPO, International Preliminary Report on Patentability for International Application No. PCT/US2006/039800 dated Apr. 16, 2008.

Yamazaki, et al., Diurnal Changes in the Composition of Abomasal Digesta in Fasted and Fed Sheep, The Tohoki Journal of Agricultural Research, Mar. 1987, vol. 37, No. 3-4, pp. 49-58.

International Search Report and Written Opinion in PCT/IE2005/000113 dated Feb. 22, 2006.

International Search Report and Written Opinion in PCT/IE2007/000050 dated Aug. 13, 2007.

The International Searching Authority, The International Search Report and Written Opinion of the International Searching Authority for International Application No. PCT/US08/63445, dated Sep. 29, 2008.

The International Searching Authority, The International Search Report and Written Opinion of the International Searching Authority for International Application No. PCT/US08/063463 dated Sep. 10, 2008.

The International Bureau of WIPO, International Preliminary Report on Patentability for International Application No. PCT/US2008/063463, dated Nov. 17, 2009, entitled "Surgical Retractor.".

The International Bureau of WIPO, International Preliminary Report on Patentability for International Application No. PCT/US08/63445, dated Nov. 17, 2009, entitled "Surgical Retractor with Gel Pad".

International Searching Authority-US, International Search Report and Written Opinion of the International Searching Authority for International Application No. PCT/US04/25511, dated Nov. 7, 2007.

The International Bureau of WIPO, International Report on Patentability for International Application No. PCT/US04/25511, dated Dec. 6, 2007.

The International Bureau of WIPO, International Preliminary Report on Patentability, for International Application No. PCT/US2012/037111, titled "Wound Retractor" dated Nov. 12, 2013.

International Search Report and Written Opinion of the International Searching Authority for PCT application No. PCT/US01/29682.

European Patent Office, The International Search Report and Written Opinion for International Application No. PCT/US2015/045058, titled "Wound Retractor," dated Nov. 12, 2015.

European Patent Office, European Search Report for European Application No. EP 10 18 9327, entitled "Split Hoop Wound Retractor," dated Dec. 14, 2010, 3 pgs.

European Patent Office, European Search Report for European Patent No. 12151288, dated Feb. 10, 2012, 8 pgs.

European Patent Office, Supplementary European Search Report for European Patent Application No. 08755322, dated Apr. 18, 2012, 3 pgs.

European Patent Office, Supplementary European Search Report for European Patent Application No. 08755336, dated Jun. 15, 2012, 2 pgs.

European Patent Office, The International Search Report and Written Opinion of the International Searching Authority for International Application No. PCT/US2016/056109, titled "Wound Retractor with Multi-Segment Outer Ring," dated Jul. 10, 2017, 36 pgs.

The International Bureau of WIPO, International Preliminary Report on Patentability for International Application No. PCT/US2015/045058, dated Feb. 23, 2017, 12 pgs.

European Patent Office, European Search Report for European Patent No. 16167739.8, dated Aug. 10, 2016, 4 pgs.

* cited by examiner

CIRCUMFERENTIAL WOUND RETRACTION WITH SUPPORT AND GUIDANCE STRUCTURES

CROSS REFERENCE TO RELATED APPLICATIONS

This application claims the benefit of U.S. Provisional Application Ser. No. 62/084,435 entitled "CIRCUMFERENTIAL WOUND RETRACTION WITH SUPPORT AND GUIDANCE STRUCTURES," filed Nov. 25, 2014.

FIELD OF THE INVENTION

The present invention relates to retraction of surgical incisions and other orifices, and more specifically to shaping and positioning a surgical incision or orifice to provide optimum access to a surgical site.

BACKGROUND

Generally speaking, the considerations involved in providing a surgical incision include adequate access to a subject area within the anatomy, minimal blood loss, maximum closure and healing potential, and minimal scaring.

Several elegant surgical incision techniques have been developed to address the foregoing. For instance the "Phannenstiel" incision used in abdominal surgery was developed to minimize the development of surgical site herniations.

With the advent of laparoscopic surgery, it has become apparent that small incisions have certain advantages. However, some surgeries present challenges that are beyond standard laparoscopic or totally open techniques. One of these is human breast surgery. In these instances, access is very important. However, aesthetic outcome is almost equally important.

Typical human breast surgery generally comprises either a periareolar incision or an inframammary incision or both. Other, more complex incision types are also available for various specific needs. For instance a triangular incision may be used where mass reduction is provided. A vertical incision may be used where maximum access is desired. Alternatively, a "b-flap" incision may be employed where specific reconstruction is indicated. This is an incision that extends from the vertical incision site to a selected lateral position. In some cases an incision is made in the umbilicus and access to breast is provided beneath the skin level.

Generally, opposing mechanical retractors are used to spread, open or enlarge an incision for appropriate access. The mechanical retractors may be moved in tandem to position the incision to maximize access and visualization. This action requires complicated and orchestrated action, usually involving two operators. An additional complication may arise when metallic retractors are employed in an environment where electrosurgical devices are in use. The potential for unintended electrical discharge is clearly present. This could result in burns that are difficult to anticipate and manage.

In view of the foregoing, there remains a need to provide surgical access to the human breast and other areas of the human body that provides acceptable access and further provides exceptional cosmetic outcome but which avoids the complications and risks of mechanical retractors.

BRIEF DESCRIPTION OF THE INVENTION

The present invention provides surgical retractor for use in a surgical incision or at a natural orifice, comprising an external support member; an internal support member; a connecting member having a distal end, a proximal end, and a tissue contacting surface, the proximal end of the connecting member connected to the external support member and the distal end of the connecting member connected to the internal support member; and a first positioning element comprising a holding portion and a connecting portion, wherein the connecting portion is attached to the external support member. In some embodiments, the connecting portion comprises a recess configured to complement the external support member such that the connecting portion may be snap fit onto the external support member to thereby attach the positioning element to the external support member. In other embodiments, the positioning element comprises a connecting feature configured such that the connecting feature may be urged over and about the external support member to thereby attach the positioning element to the external support member. In still other embodiments, the positioning element comprises a cut-out area and defines an opening sized and configured to slide past the connecting member so that the cut-out area may engage the external support member to thereby attach the positioning element to the external support member.

Optionally, the surgical retractor further comprises a support structure, the support structure having a base and a pivot point, wherein the base is configured to attach to a surgical table and the pivot point is configured to attach to the holding portion of the positioning element.

In some embodiments, a second positioning element may attached to the external support member. Optionally, the surgical retractor may also comprise a first support structure and a second support structure, each support structure having a base and a pivot point, wherein the bases are configured to attach to a surgical table, the pivot point of the first support structure is attached to the first positioning element and the pivot point of the second support structure is attached to the second positioning element.

In some embodiments, the internal support member comprises an inflatable toroid, the inflatable toroid being connected to a transfer conduit configured to interact with a gas or fluid supply. In other embodiments, the internal support member comprises a memory foam, the internal support member configured to be deformed for insertion through an incision, returning to a predetermined shape once within the surgical field.

In other embodiments, the surgical retractor comprises an external support member; an internal support member; a connecting member having a distal end, a proximal end, and a tissue contacting surface, the proximal end of the connecting member connected to the external support member and the distal end of the connecting member connected to the internal support member; a seal cap, the seal cap comprising a cap ring and an elastomeric seal disposed within the cap ring, wherein the cap ring is configured to sealingly engage the external support member, the cap ring comprising an attachment feature; and a first positioning element comprising a holding portion and a connecting portion, wherein the connecting portion is configured to detachably engage with the attachment feature. Optionally, the attachment feature comprises a series of tabs and grooves configured to form a complementary fit with the connecting portion of the positioning element. In some embodiments, a second positioning element may be configured to detachably engage with the attachment feature.

In some embodiments, the elastomeric seal comprises at least one access port. In other embodiments, the elastomeric seal further comprises at least one receptacle and at least one insert configured to fit in the receptacle.

In some embodiments, a surgical retractor comprises an external support member; an internal support member; a connecting member having a distal end, a proximal end, and a tissue contacting surface, the proximal end of the connecting member connected to the external support member and the distal end of the connecting member connected to the internal support member; and an external support structure, wherein the external support structure comprises an adjustable neck attached to a table stand, the adjustable neck configured to detachably attach to the external support member. Optionally, the adjustable neck comprises a first arm segment, a second arm segment and a hinge, the hinge connecting the first arm segment and the second arm segment.

In one embodiment useful when insufflating cavities within the body, the retractor comprises an external support member; an internal support member; a connecting member having a distal end, a proximal end, and a tissue contacting surface, the proximal end of the connecting member connected to the external support member and the distal end of the connecting member connected to the internal support member; a pressure sensitive seal, the seal comprising a cylindrical body, a movable sealing member, a compression spring disposed within the cylindrical body, the compression spring configured to engage the movable sealing member, and a cap having at least one opening, the cylindrical body comprising a first open end configured to attach to the external support member, a second open end attached to the cap, a first portion positioned near the first open end, the first portion having a smooth interior surface, and a second portion positioned near the second open end, the second portion having a fenestrated interior surface, wherein the opening in the cap is aligned with at least one fenestration and the sealing member is configured to move within the cylindrical body in response to pressure changes, from a low pressure state in which the sealing member is positioned within the first portion to sealing engage the smooth interior surface to a high pressure state in which the sealing member is forced upward by insufflation gases against the compression spring into the second portion having a fenestrated interior surface, thereby allowing the insufflation gas to escape through the opening in the cap and returning the sealing member to the low pressure state. Optionally, the cap is axially or radially adjustable to modulate the pressure of the insufflation gas.

In still another embodiment of the present invention, the surgical retractor is illuminated, comprising an external support member; an internal support member; a connecting member having a distal end, a proximal end, and a tissue contacting surface, the proximal end of the connecting member connected to the external support member and the distal end of the connecting member connected to the internal support member; a positioning element comprising a holding portion and a connecting portion, wherein the connecting portion is attached to the external support member; and an illumination element attached to the internal support member. In some embodiments, the illumination element comprises a flexible fiber-optic bundle disposed within a tubular structure and connected to a light source by a fiber option cable. In other embodiments, the illumination element comprises light emitting diodes ("LEDs") disposed with a tubular ring, the LEDs connected to an energy source by an electrical conduit.

Optionally, the illuminated element is attachable to and detachable from the interior support member. In some embodiments, the illuminated surgical retractor comprises a reflective surface on the illumination element, configured to reflect light into the surgical field.

These and other features of the invention will become more apparent with a discussion of the various embodiments in reference to the associated drawings.

DETAILED DESCRIPTION OF THE PREFERRED EMBODIMENTS

The present invention describes a circumferential incision retractor or wound retractor and a supporting, manipulating or positioning tool that detachably attaches to the circumferential retractor. Optionally, a sealing member associated with an external member of the retractor and/or an external support structure may be used with the manipulating tool or member as needed. The disclosed embodiments are described with reference to their use in human breast surgery, although they may be used as appropriate in other surgical procedures, particularly where cosmetic outcome is important. It should also be appreciated that the described retractor may also be used in natural orifices where appropriate.

Figure 1:
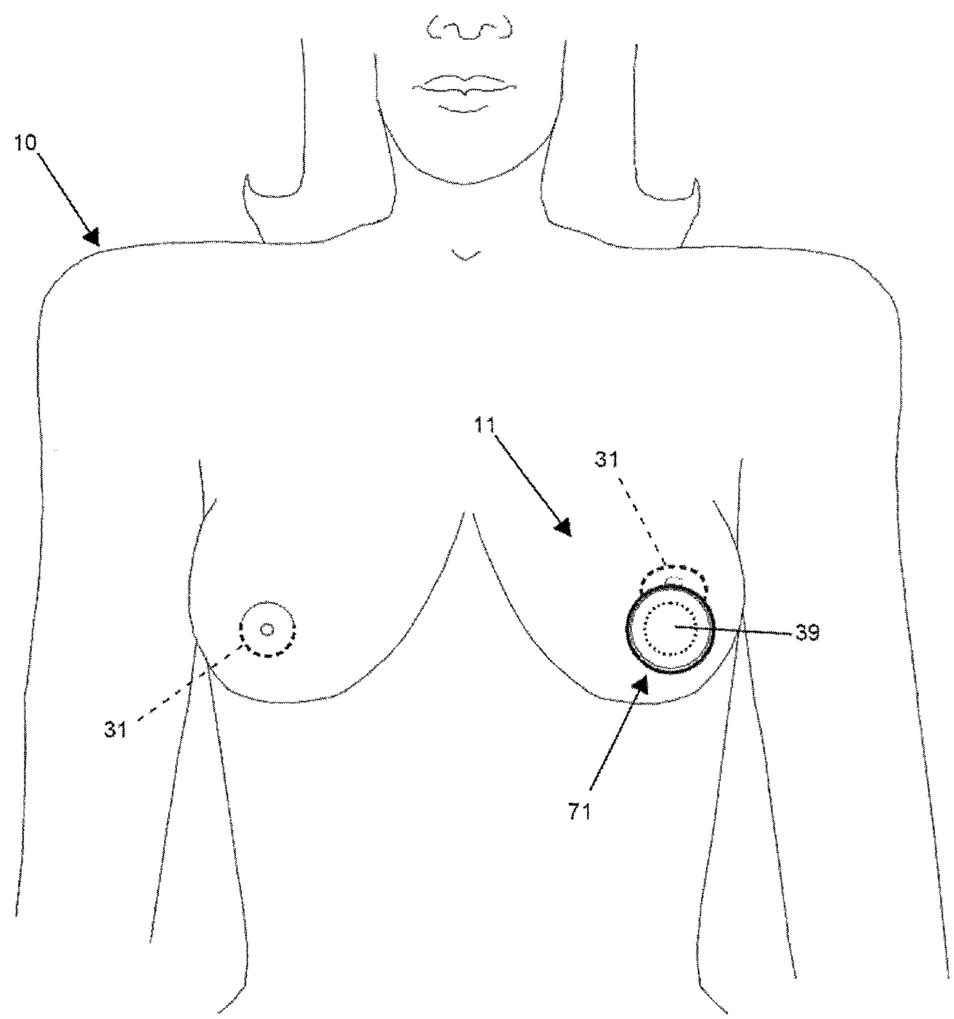
FIG. 1 illustrates a first use of a circumferential retractor involving a human breast in a periareolar incision.
Figure 2:
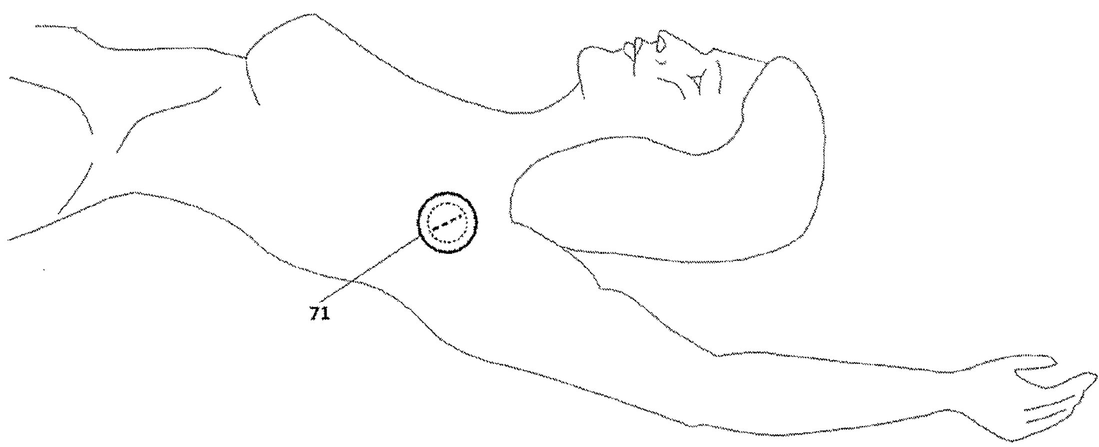
FIG. 2 is a lateral view of a transaxillary incision where a circumferential retractor is placed within said incision.

FIG. 1 shows a female human torso 10 in a supine position with a periareolar skin incision 31 made in the breast 11 to gain access to the interior tissue. A circumferential retractor 71 according to the present invention is placed within the incision 31 and deployed to reshape and shield the initial incision as desired. The circumferential retractor acts on the initial incision to produce an enlarged opening 39 through which surgical instruments may be inserted. Deployment of a circular retractor 71 in a transaxillary incision is shown in FIG. 2.

Figure 3:
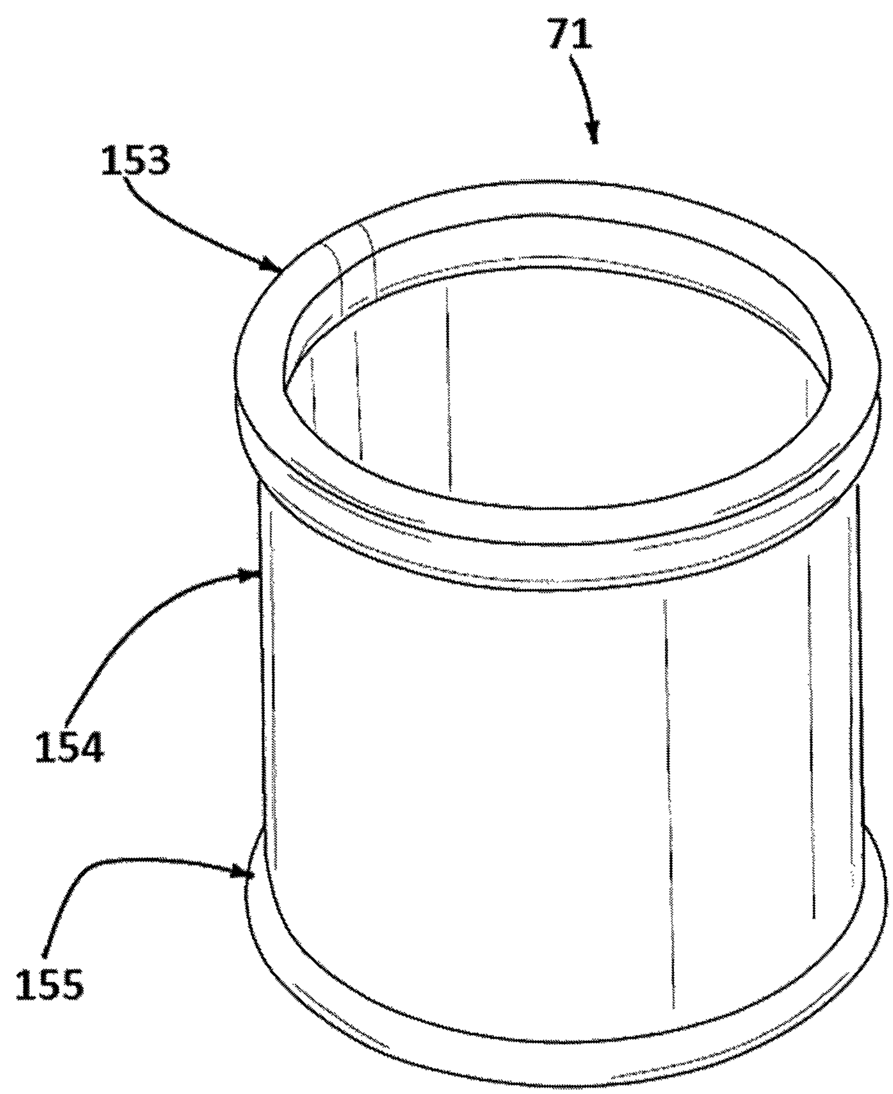
FIG. 3 is a perspective view of a circumferential retractor.

Surgical instruments may be inserted and used through the retractor 71 and the modified incision 31 as desired. In a preferred embodiment, shown in FIG. 3, the circumferential retractor 71 comprises a first, internal support member 155, a second, external support member 153 and a cylindrical connecting member 154. The connecting member 154 comprises an external tissue-contacting surface and an internal surface that, when deployed, lines an access opening into the body. The connecting member 154 is preferably sized and configured to present a circumferential outward force or pressure upon tissue through which it has been inserted as it is acted upon by activity associated with an external support member 153. More simply stated, as the external support member 153 is rotated upon itself, the attached connecting member 154 is shortened linearly. As the connecting member 154 is shortened, the tissue through which it has been inserted is forced away from the axis of the device 71. The result of the force upon the tissue is an enlarged opening 39 through which a surgical procedure may be performed.

It should be noted that the particular configuration of the internal and external support members may be varied depending on particular use. For example, the support members are shown as circular rings but may have other shapes, such as oval or semicircular. Also, the support members may occur singly or in some multiple as, for example, a double-ring external support member. The support members may be solid or hollow, flexible or rigid. Suitable circumferential retractors are described in U.S. Pat. Nos. 7,650,887, 7,727,146 and 7,704,207, the disclosures of which are incorporated by reference in their entireties.

Figure 4A:
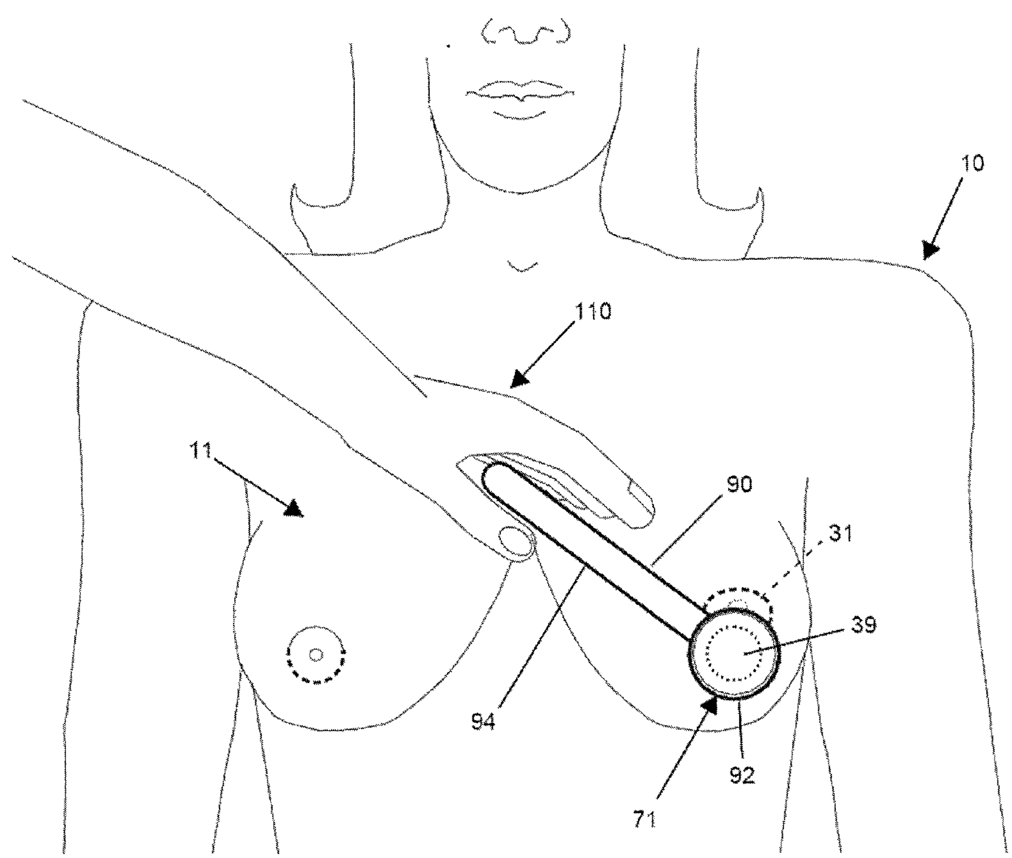
FIG. 4A is a top view of a circumferential retractor with an attached positioning or manipulating element, deployed in a periareolar incision.
Figure 4B:
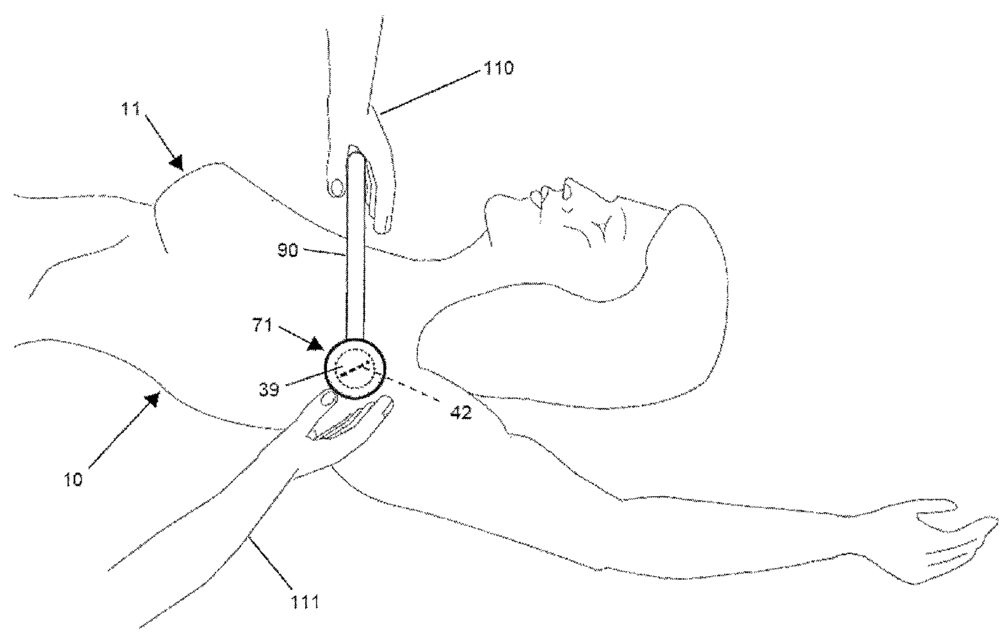
FIG. 4B is a top view of a circumferential retractor with an attached positioning or manipulating element, deployed in a transaxillary incision.

In FIG. 4A, a female human torso 10 is shown with a periareolar incision 31 in the breast 11, into which a circumferential retractor 71 has been placed to create an enlarged opening 39. Once the circumferential retractor 71 is appropriately placed, a first positioning element 90 may be placed upon the external support member 153 and used to maneuver the retractor 71 as desired. The first positioning 90 may preferably comprise a connecting portion 92 and a holding portion 94. The connecting portion 92 may be sized and configured to attach to the external support member 153 in a way that it can be rotated about the central axis of the device 71. The positioning element 90 may additionally be configured to be held by a human hand 110. In FIG. 4B, a female human torso 10 is shown with a transaxillary incision 42 in the breast 11, into which a circumferential retractor 71 with a positioning element 90 has been placed to create an enlarged opening 39.

In a preferred embodiment, a positioning element 90 associated with the retractor 71 of the present invention may be rotated 360 degrees around the central axis of the circumferential retractor 71 without presenting rotational forces upon the associated tissue. The positioning element 90, once attached to the external support member 153, may be used to maneuver or position the retractor 71 to a preferred orientation or position.

Figure 5A:
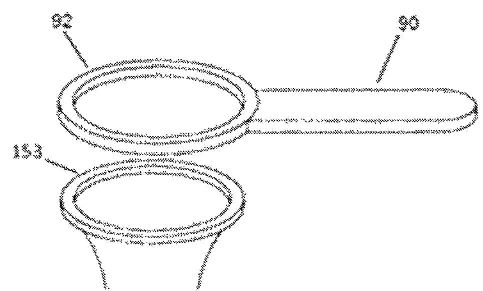
FIG. 5A is a perspective view of a positioning element adapted to snap over an outer ring.
Figure 5B:
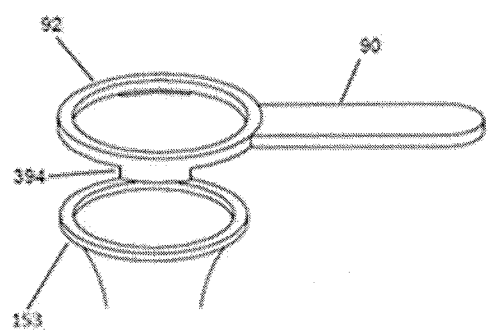
FIG. 5B is a perspective view of a connecting feature adapted to attach to an external support structure.
Figure 5C:
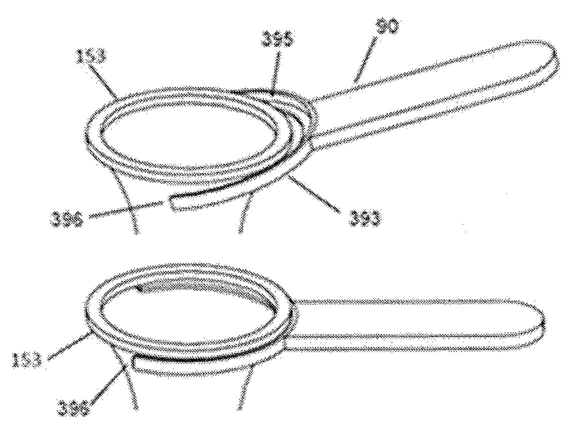
FIG. 5C is a perspective view of a positioning element with a cut-out area configured to engage an external support member.

With reference to FIGS. 5A-5C, one or more positioning elements 90, 91 may be attached to the external support member 153 in a variety of ways. A first positioning element 90 may be snapped over the outer ring or external support structure 153 so that the structure is contained within an undercut in the connecting portion 92 that allows axial rotation of the handle 90 about the axis of the circumferential retractor (FIG. 5A). An alternate embodiment, shown in FIG. 5B, makes use of at least one connecting feature 394 positioned on the connecting portion 92 that may be urged over and about the external support structure 153. An additional embodiment makes use of a positioner 90 having a connecting portion 393 with an opening 396 sized and configured to slide past the cylindrical connecting member 154 and then upward so that a cut-out area 395 of the connecting portion 393 may engage the external support member 153 (FIG. 5C).

With a positioning element attached to the circumferential retractor, an operator may manipulate the incision or wound from its initial position to a first preferred position or a second preferred position depending on the particular surgical needs. Performing such manipulation with the present invention reduces trauma to the incision site than conventional mechanical retractors and provides a more open operative space.

Figure 6A:
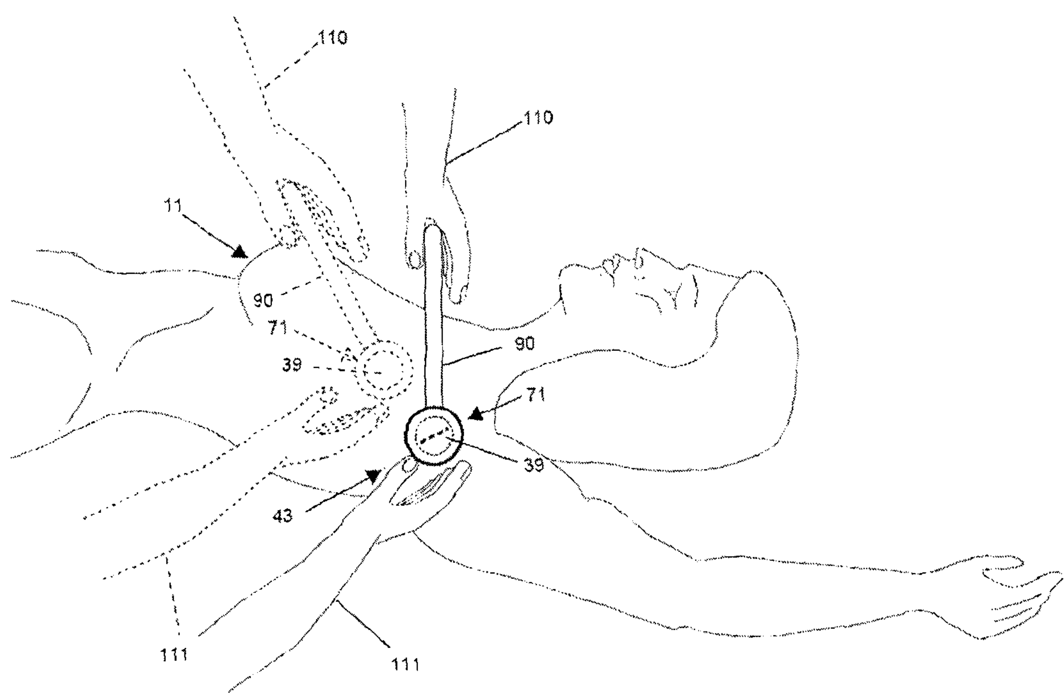
FIG. 6A is a lateral view of a transaxillary incision where a circumferential retractor is placed within said incision and a positioning member is attached and maneuvered to first preferred position.
Figure 6B:
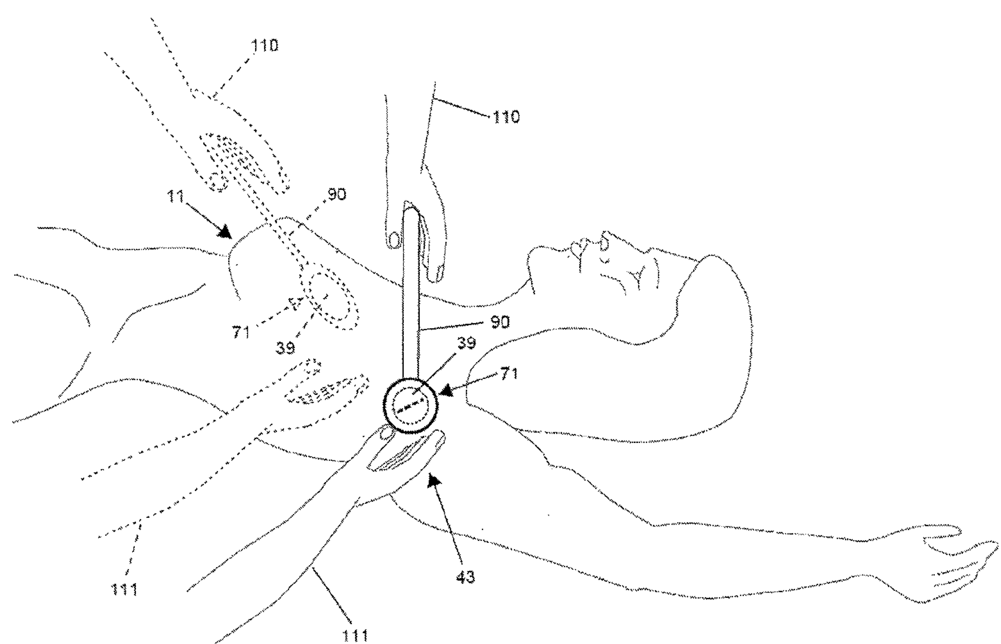
FIG. 6B is a lateral view of a transaxillary incision where a circumferential retractor is placed within said incision and a positioning member is attached and maneuvered to a second position.

FIG. 6 shows a lateral view of a transaxillary incision 43 where a circumferential retractor 71 is placed within said incision and a positioning member 90 is attached and maneuvered to first preferred position (FIG. 6A, shown with broken lines) and to a second preferred position (FIG. 6B, shown with broken lines). A second operative hand 111 is free to deploy medical instruments (not shown) through the enlarged opening 39 at any of the positions.

Figure 7:
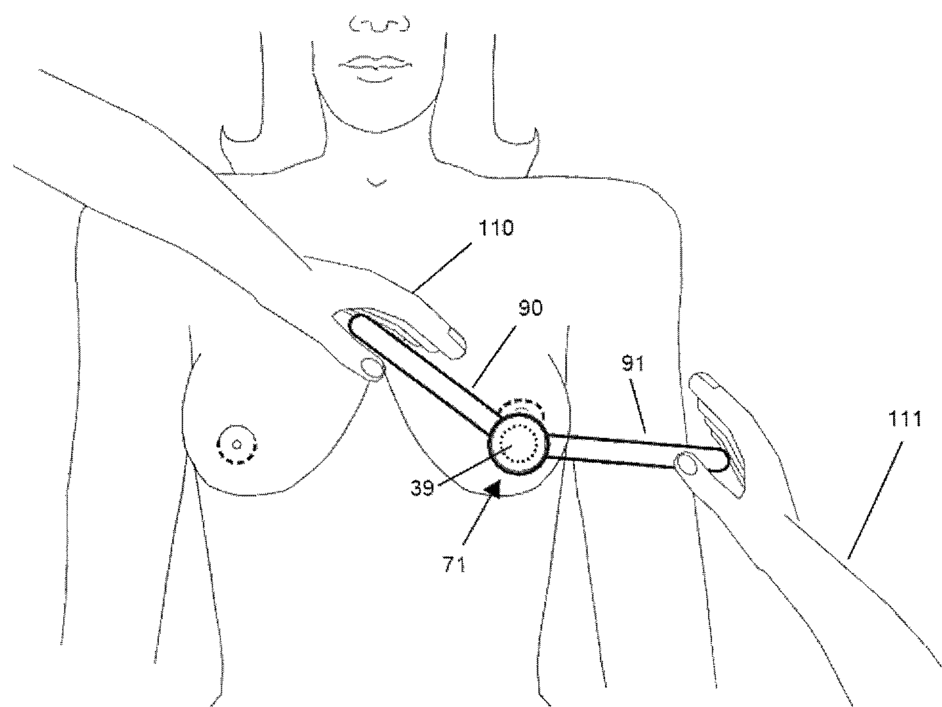
FIG. 7 illustrates the circumferential retractor of FIG. 4A with a second attached positioning or manipulating element.

In a further preferred embodiment, shown in FIG. 7, a second positioning element 91 may be attached to the external support member 153 in a similar manner as the first positioning element 90. The thusly attached positioning elements 90, 91 may be rotated independently about the central axis of the circumferential retractor 71.

Figure 8A:
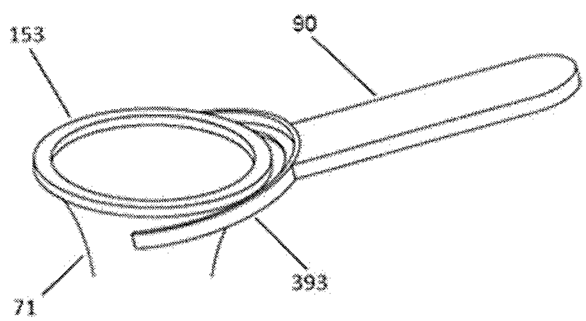
FIG. 8A is a perspective view of a retractor having a first and a second positioning element with the first positioning element placed under an external support structure.
Figure 8B:
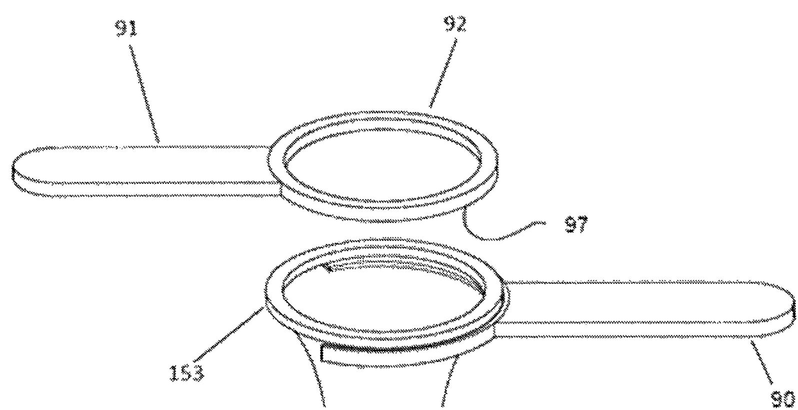
FIG. 8B is a perspective view of a retractor having a first and a second positioning element, with the second positioning element comprising an engaging feature adapted to attach to the first positioning element.
Figure 8C:
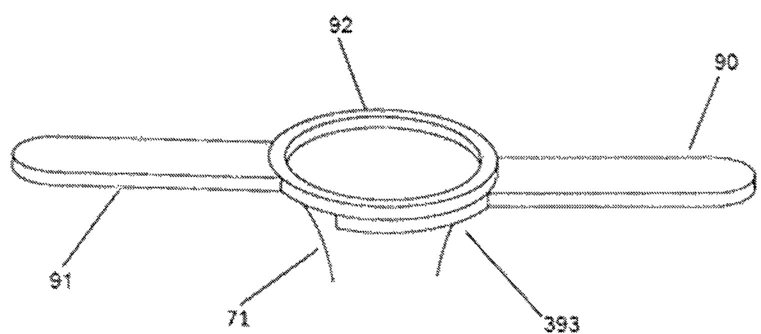
FIG. 8C is a perspective view of a retractor having a first and a second positioning element, with the second positioning element configured to attach to an open connecting portion of the first positioning element.

Referring now to FIGS. 8A-8C, one embodiment of a scheme to attach two positioning elements to the external support structure 153 comprises a first positioning element 90 having an open connecting portion 393 placed under the external support structure 153 (FIG. 8A) and a second positioning element 91 that may be attached to the first positioning element 90 thereby capturing the external support structure 153 for maneuvering. A preferred embodiment of the second positioning element 91 comprises one or more engaging features associated with the underside 97 of the generally circular connecting portion 92 of the positioning element 91 (FIG. 8B), sized and configured to attach to the open connecting portion 393 of the first positioning element 90 (FIG. 8C). Engaging features may include, for example, tabs and detents, hooks and lattices, and the like.

Figure 8D:
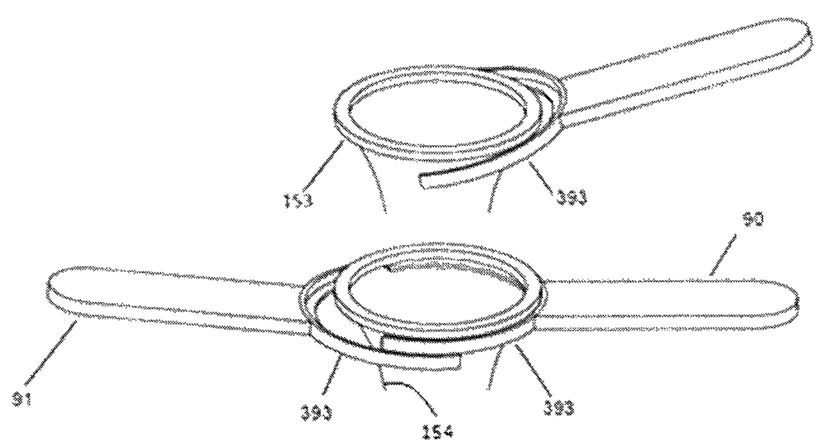
FIG. 8D is a perspective view of a retractor having a first and a second positioning element, with the first and second positioning elements configured to slide past the cylindrical connecting member to upwardly engage an external support member.

Any combination of the embodiments shown in FIG. 5 may also be used to attach two positioning elements 90, 91 to the external support structure 153. For example, the first positioning element 90 may be snapped over the external support member 153 as in FIG. 5A, while the second positioning element 91 may include a connecting portion 393 configured to attach as shown in FIG. 5C. In FIG. 8D, both positioning elements attach by sliding past the cylindrical connecting member 154 and upward to engage the external support member and/or the other positioning element.

Figure 9:
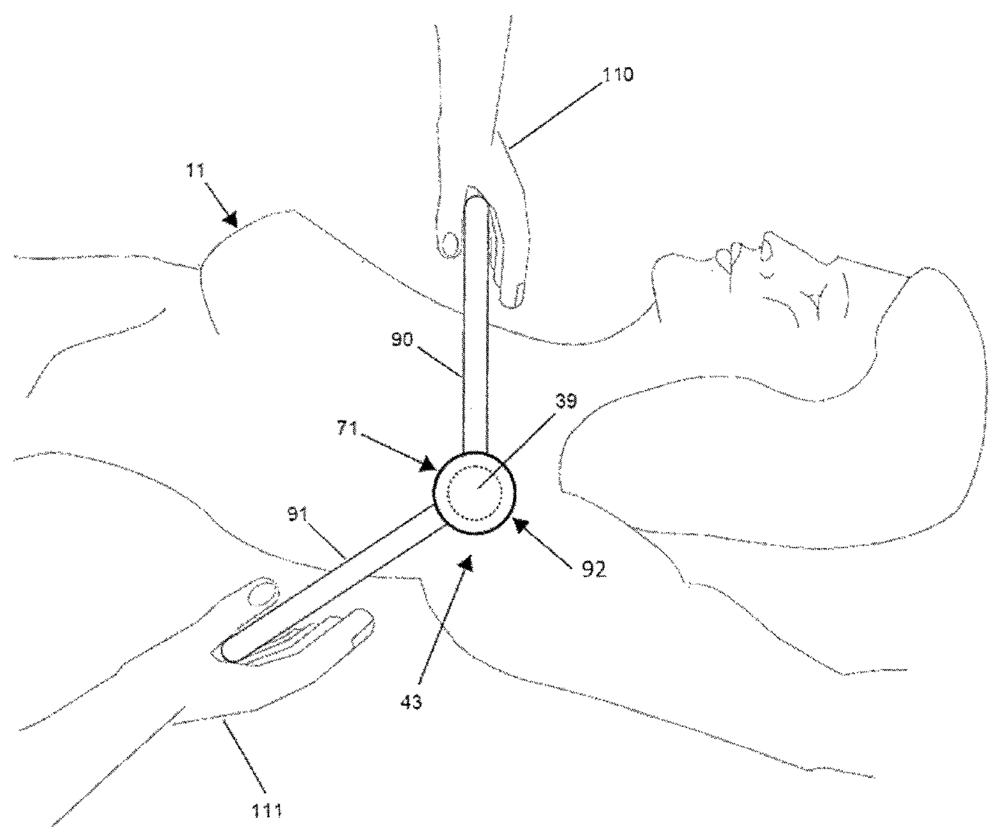
FIG. 9 is a lateral view of a transaxillary incision illustrating the use of more than one positioning element.
Figure 10:
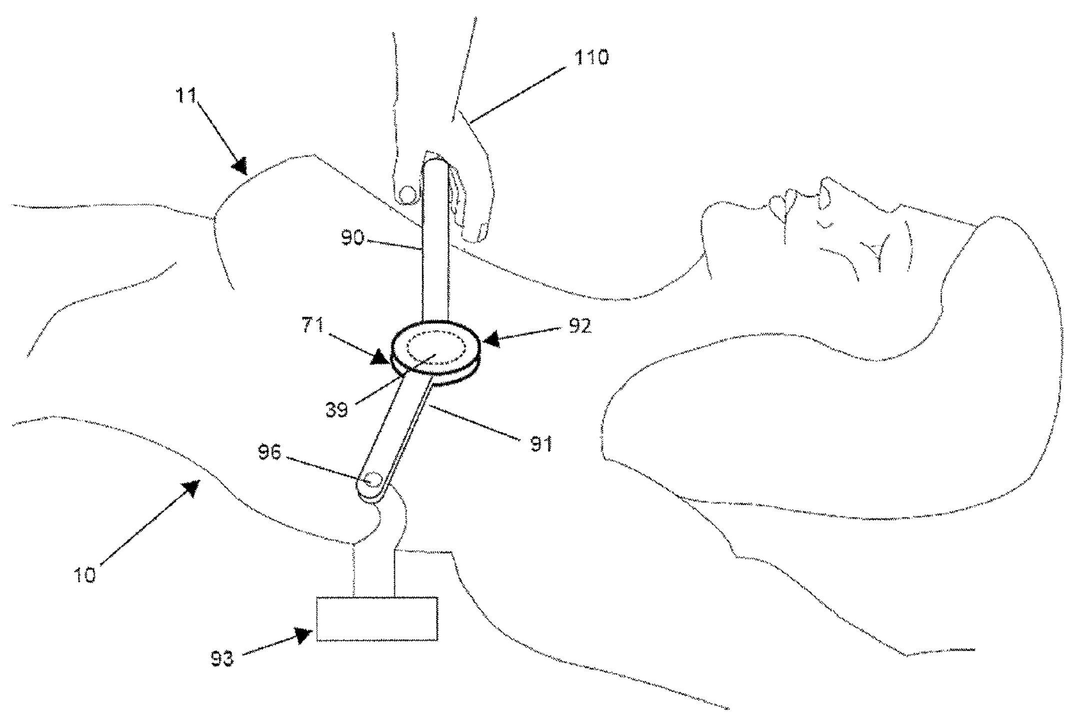
FIG. 10 is a lateral view of a transaxillary incision illustrating the use of more than one positioning element and a stabilizing member.

Referring to FIGS. 9 and 10, a preferred embodiment may comprise a first positioning element 90 that may be held with one hand 110 of a first operative individual and a second positioning element 91 that may be held with one hand 111 of a second operative individual. The cooperative action of the two associated positioning elements 90, 91 allows extreme manipulation of the retractor 71. In an alternate preferred embodiment, a first 90 or second 91 positioning element may attach to a support structure 93 associated with a surgical platform such as an operating table. In this instance, the attachment of a positioning element provides a pivot point 96 or fulcrum so that manipulation and positioning of the retractor 71 may be accomplished by a single hand. A second support structure may be employed to attach to either a first or second positioning element 90, 91 so that an associated retractor may be positioned and held in place as desired. It is important to note that while the present device is depicted for use in the axillary region 43, it may be used in other surgical site locations as well.

A preferred embodiment of the present invention, shown in FIGS. 11-15, may further comprise an external attachment member or seal cap 157 that is sized and configured to provide a gas-tight seal at the outer, external, proximal portion of the retractor 71. The gas-tight seal allows positive pressurization of an anatomical region associated with the distal or internal portion of the circumferential retractor 71. A preferred gas-tight seal cap 157 may comprise a cylindrical elastomeric member sized and configured to fit securely upon an external support member 153 associated with a circumferential retractor 71.

Figure 11:
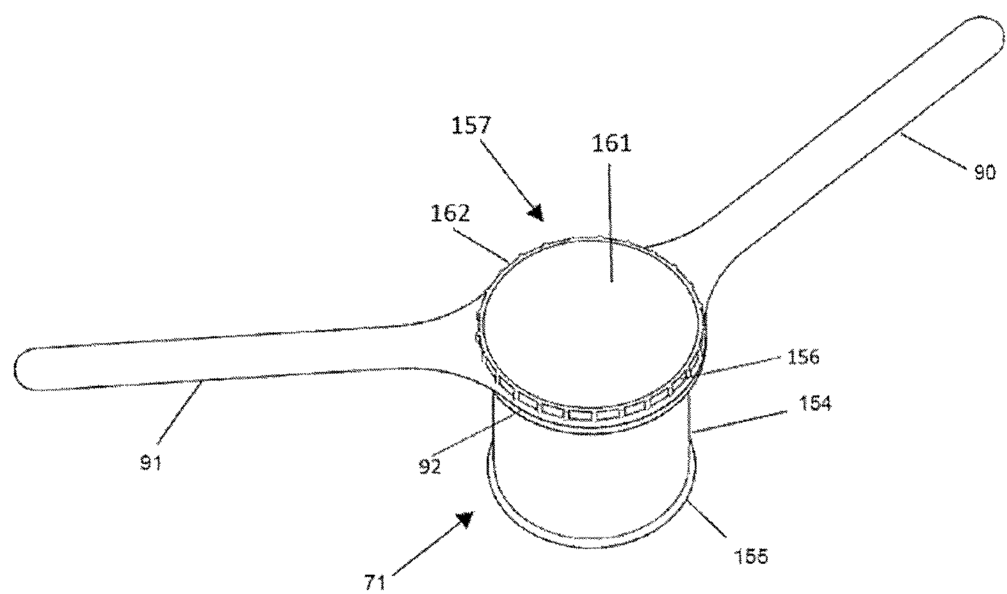
FIG. 11 is a perspective top view of a circumferential retractor having two positioning members and a seal cap.
Figure 12:
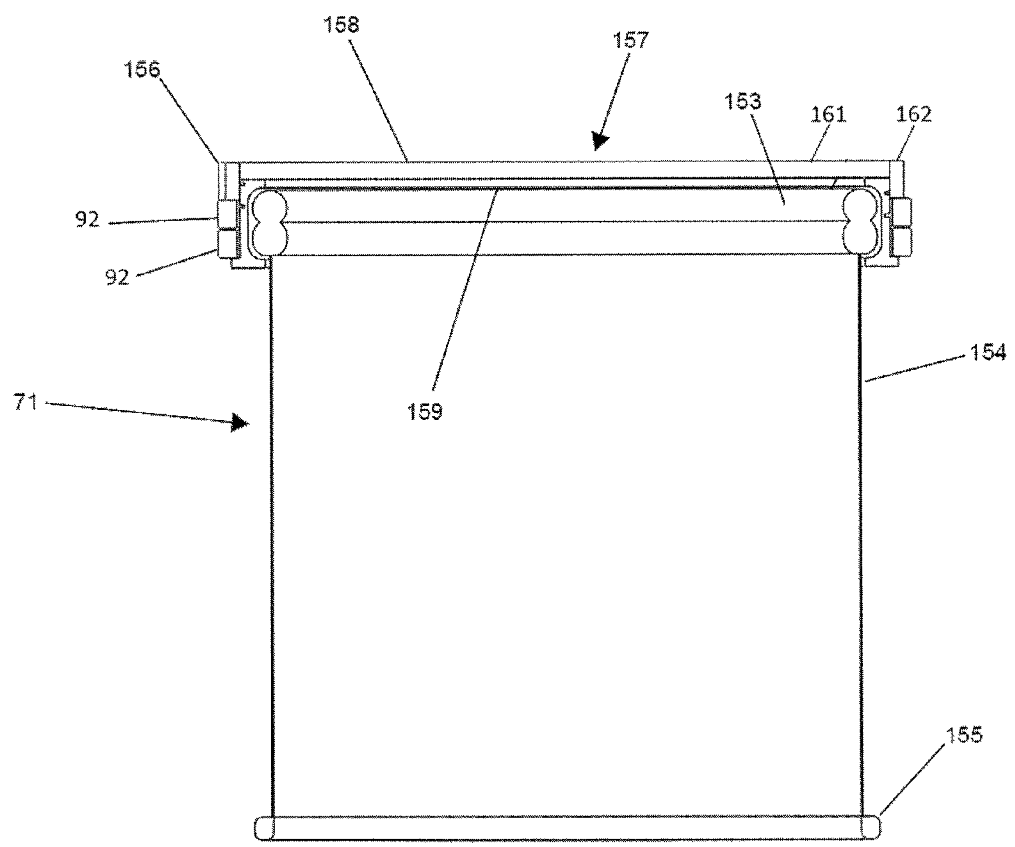
FIG. 12 is a side-section view of the circumferential retractor of FIG. 11.

For example, as seen in FIGS. 11-12, an elastomeric seal member or cap 157 according to the present invention comprises a disk-shaped portion 161 having a diameter, a thickness, a first surface 158, a second surface 159 and cap ring 162 configured to hold the disk-shaped elastomeric seal portion. Preferably, the cap ring further comprises an attachment feature 156. Attachment feature 156 may be configured to detachably interact with the connecting portion 92 of one or more positioning elements 90, 91. For example, the attachment feature may be a series of alternating tabs and grooves which form a complementary fit with the connecting portion.

Figure 13:
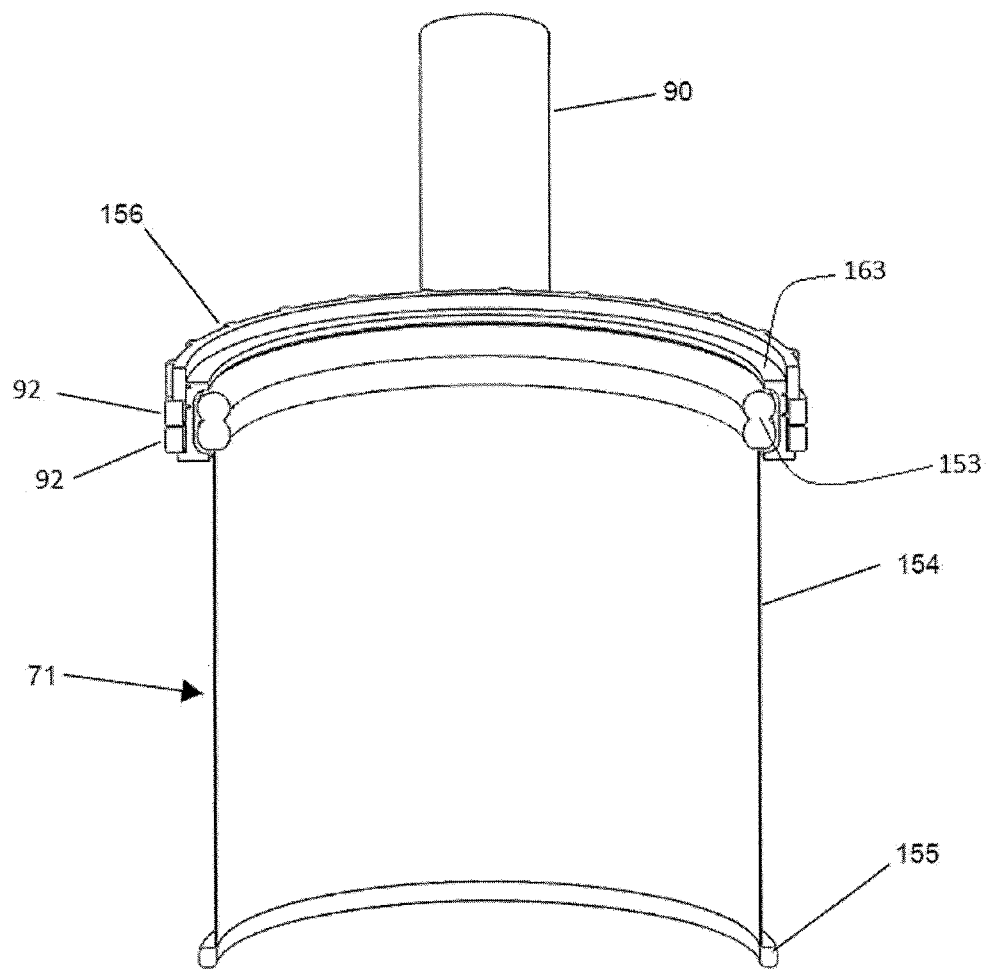
FIG. 13 is an oblique side-section view of the circumferential retractor of FIG. 11, which the elastomeric seal portion removed.

FIG. 13 shows the retractor plus seal cap of FIG. 12 in oblique view, with the disk-shaped portion removed to show a circumferential ledge 163, which supports the disk-shaped elastomeric seal member within the cap ring 162. As shown in FIG. 13, the cap ring attaches to the external support member 153 of the retractor.

In a preferred embodiment, the elastomeric seal member 157 is highly flexible or, at least, made from a soft, compliant material such as styrene-block-copolymer or silicone rubber. In a first embodiment, a surgical tool or instrument may be passed through the material and into a body cavity. In a second embodiment, a surgical tool or instrument may be passed through an access port 167 associated with the elastomeric seal member 157 and into a body cavity.

Figure 14:
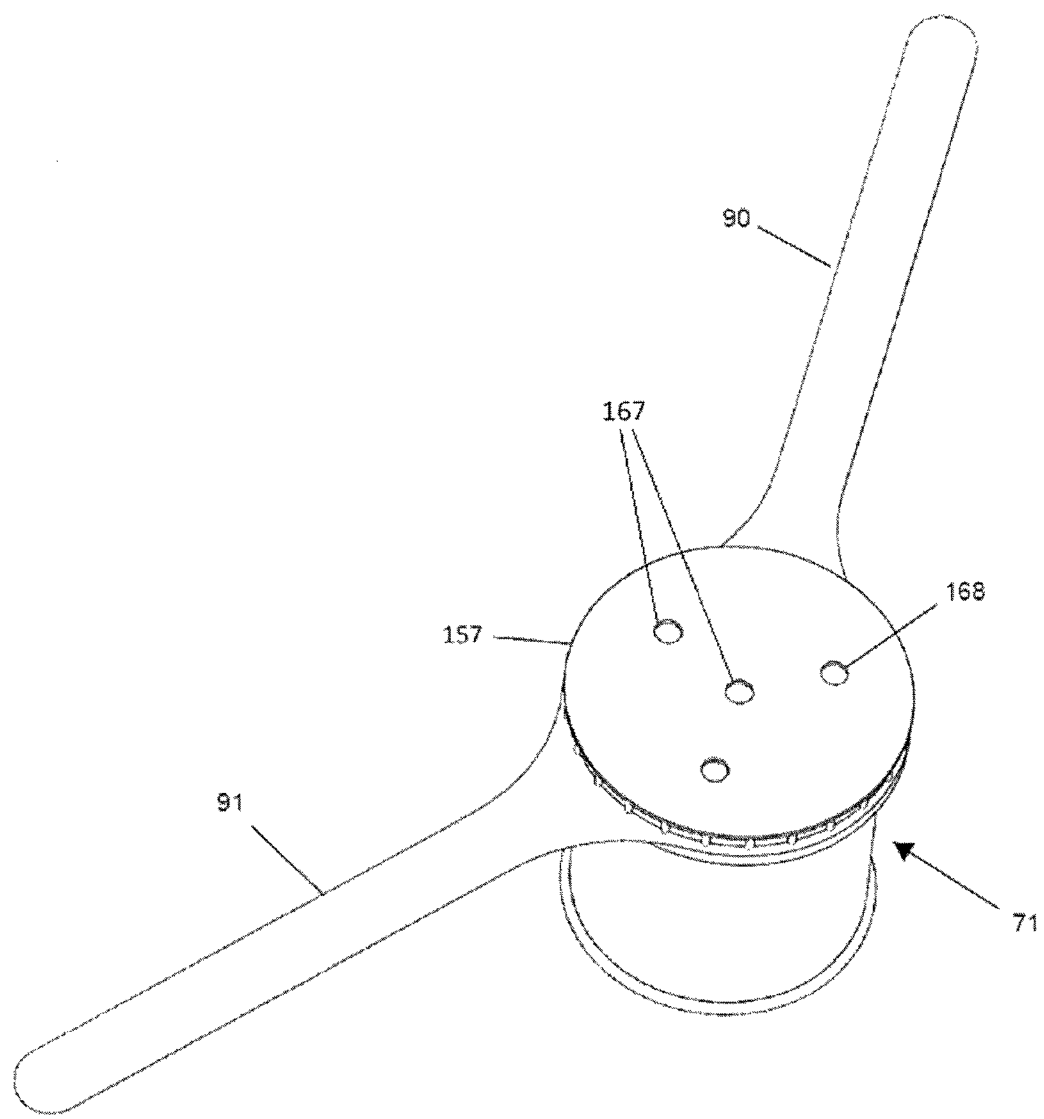
FIG. 14 is a perspective top view of a circumferential retractor having two positioning members and a seal cap with dedicated instrument seals.
Figure 15:
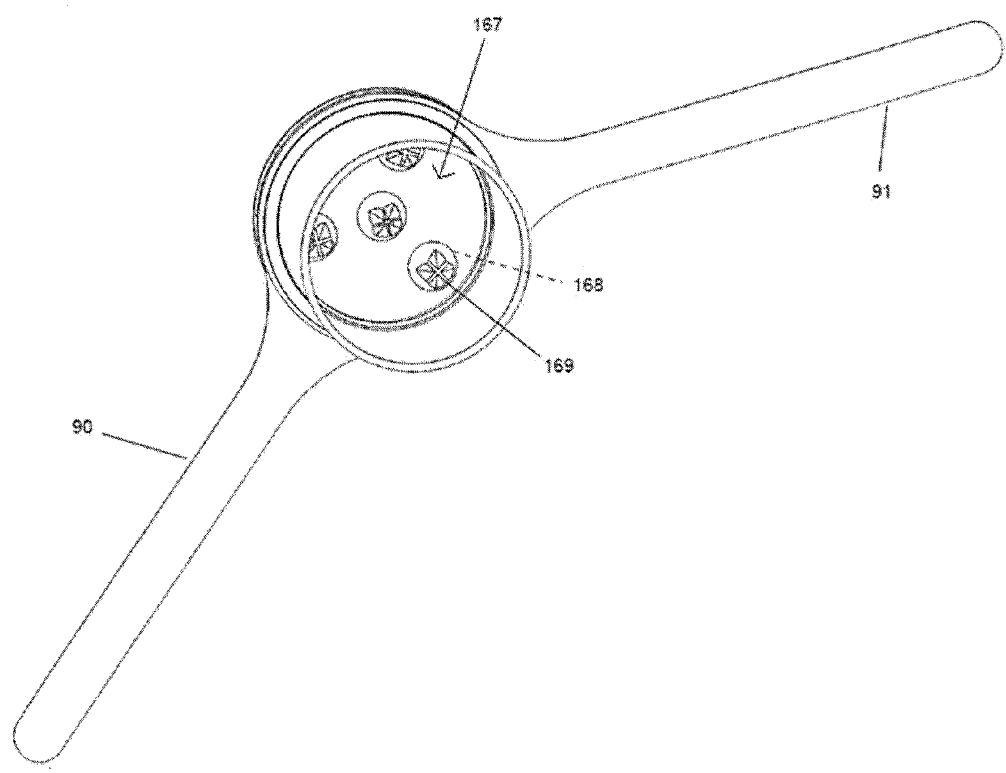
FIG. 15 is a perspective bottom view of a circumferential retractor having two positioning members and a seal cap with dedicated instrument seals.

The elastomeric member or cap 157 may additionally be configured to accept the passage of surgical tools or instruments while preventing depressurization of an internal area, as shown in FIGS. 14-15. The elastomeric seal member 157 may further comprise one or more individual sealing access ports 167. Each of the individual access ports may further comprise a septum 168 and a check valve 169. The individual access ports 167 may be sized and configured to respond to surgical tools or instruments within a range of nominal sizes.

Figure 16:
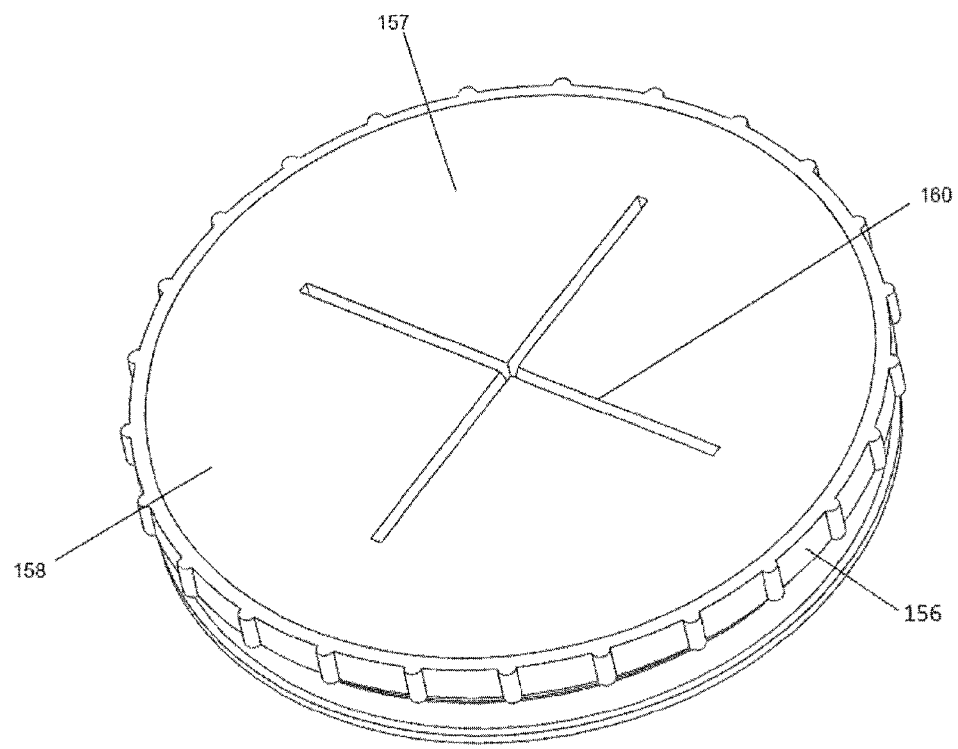
FIG. 16 is an oblique top view of a seal cap according to one aspect of the present invention where flat instruments may be used.
Figure 17A:
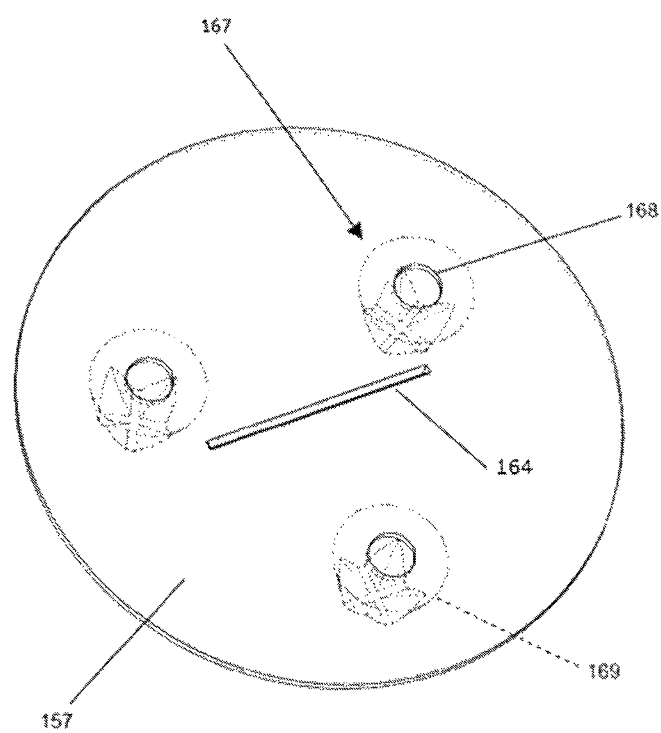
FIG. 17A is a top-side detailed view of a seal cap having various individual access ports.
Figure 17B:
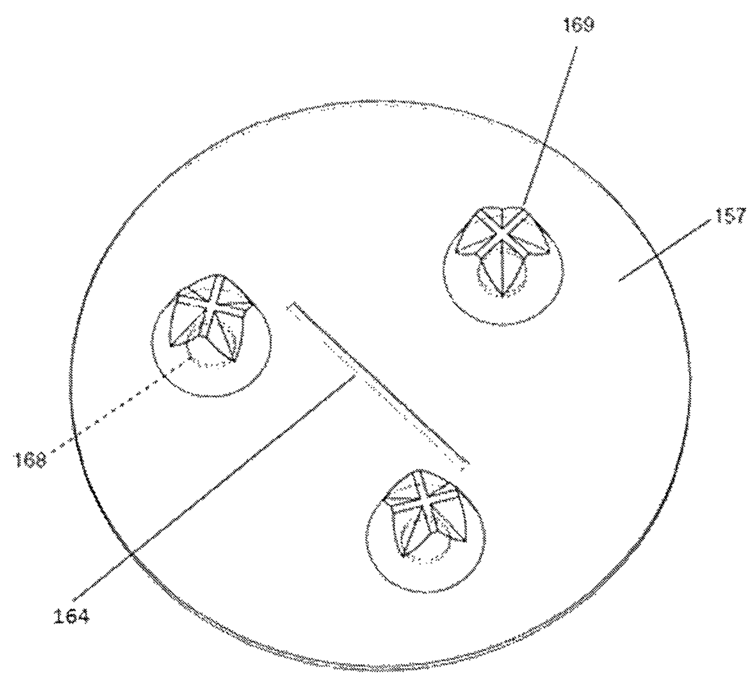
FIG. 17B is a bottom-side detailed view of the seal cap of FIG. 17A.

For purposes of construction, the individual access ports 167 associated with the elastomeric seal 157 member may be integrally formed. The present invention contemplates that the individual access ports 167 may be sized and configured for larger or smaller instruments according to the demands of a specific procedure. In addition, a specific procedure may call for an irregularly shaped instrument. Therefore, the elastomeric seal member 157 and individual access ports 167 may be adapted or manufactured to accommodate the tools, devices or instruments associated with a specific procedure. For instance, an elastomeric seal member 157 designed for use in breast surgery may comprise two or more access ports 167 sized and configured for surgical instruments having a five millimeter shaft-diameter. In addition, one port may accommodate a telescope having a shaft diameter of eight millimeters or more or less. In addition to the foregoing, an additional access port 160, 164 may be sized and configured to accommodate a generally flat-shaped instrument, such as a dissecting probe or otherwise spatulated instrument, as shown in FIGS. 16 and 17A,B.

Figure 18:
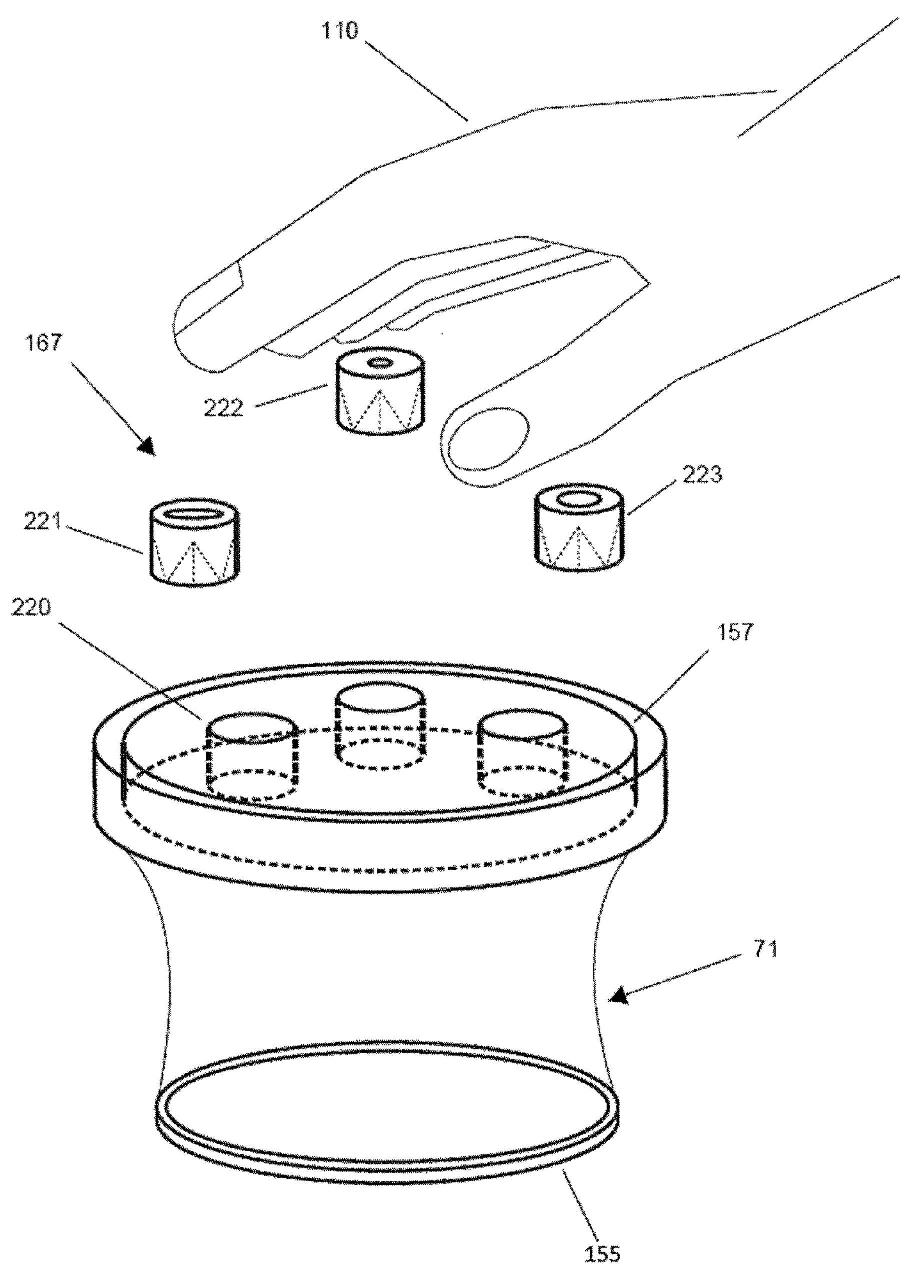
FIG. 18 illustrates a circumferential retractor having a seal-cap and a plurality of removable or exchangeable access port inserts.

Now referring to FIG. 18, an alternate construction according to the present invention comprises one or more individual access ports 167 that are exchangeable according to the procedural needs of a specific surgery. For instance, a small-bore insert 222 may be placed within the elastomeric seal cap 157 as needed. Next, an insert 223 having a larger bore may be placed as needed. An additional insert 221 having different characteristics than the first two inserts may be placed. In other words, the present invention contemplates a variety of individual seal inserts that may be selected as required and placed within receptacles 220 within the seal cap 157.

Figure 19:
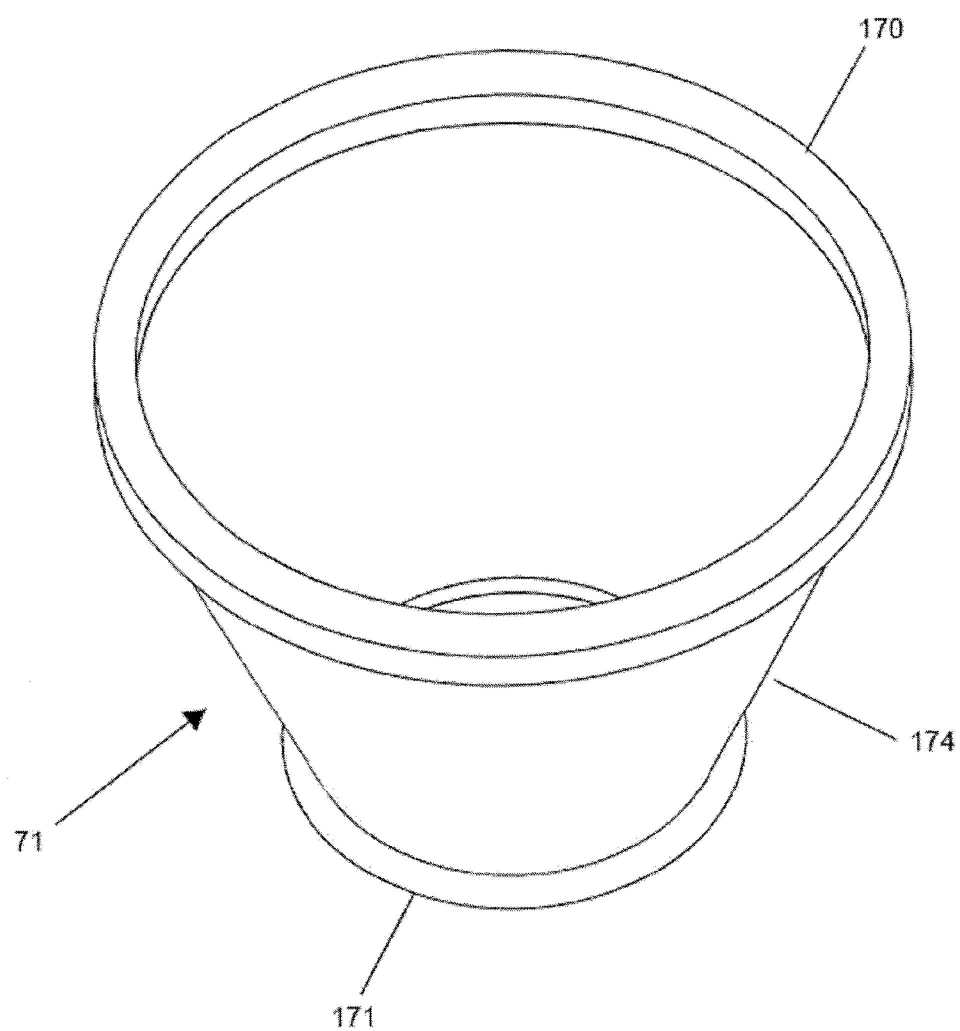
FIG. 19 is an oblique view of an embodiment of a circumferential retractor having a tapered connecting member or sleeve.

As discussed above, the present invention may be used in a variety of surgical scenarios, although it does have particular use in breast surgery. Some surgical procedures, including breast surgery, may require considerable lateral retraction while still keeping the incision as small as possible. Also, some surgical sites may have limited space in which to anchor the internal support structure, a situation very different from abdominal surgery, for example. In such instances, a preferred embodiment of the present invention further comprises an internal support structure that may be significantly smaller than the outer support structure, as seen in FIG. 19. In this embodiment, the connecting member 174 is frustoconical in shape, connecting a smaller internal support member 171 to a larger external support member 170.

Figure 20:
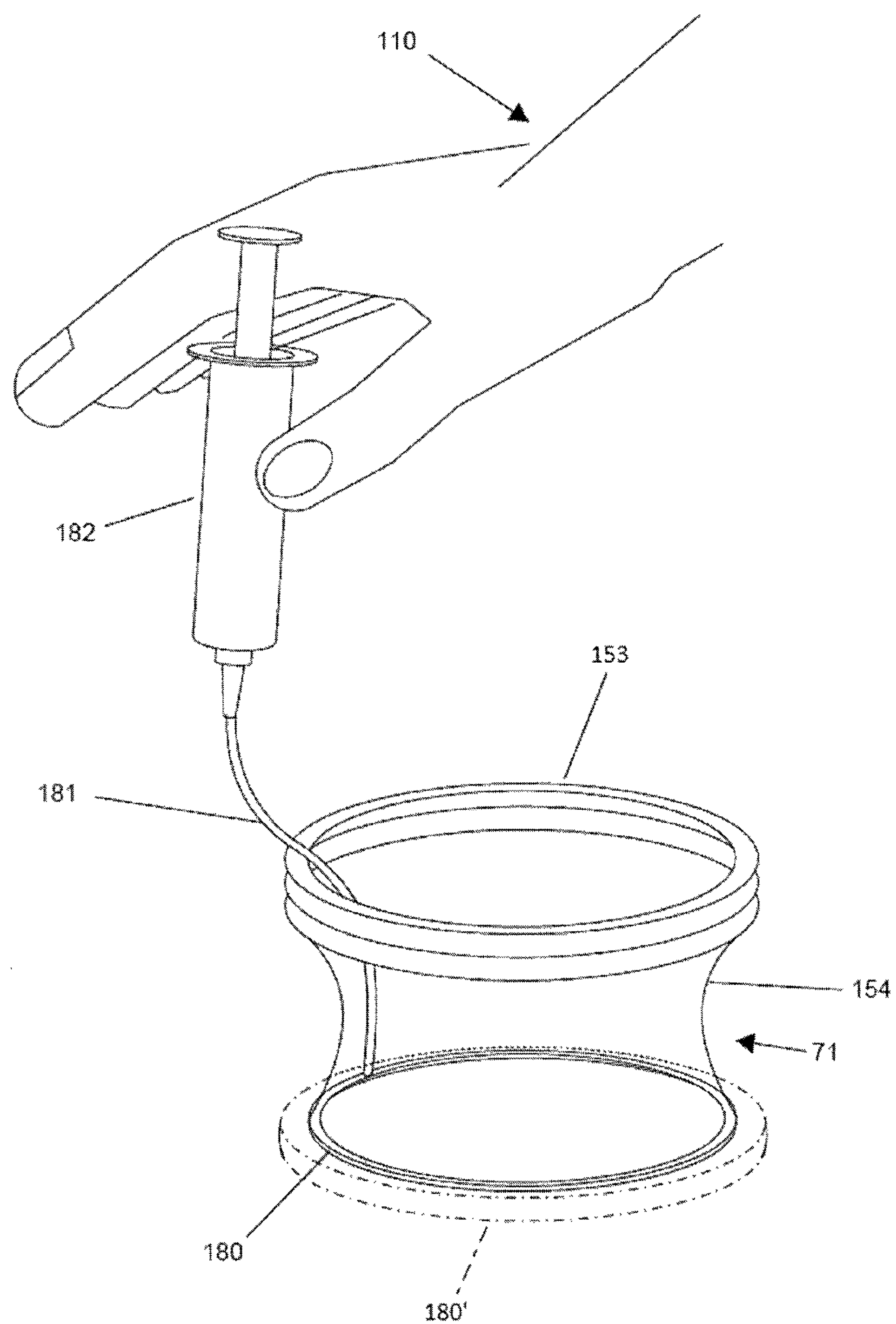
FIG. 20 is a perspective view of a circumferential retractor having an inflatable inner support member, shown in a first, uninflated condition (solid) and a second, inflated condition (broken).

Referring now to FIG. 20, an inflatable distal or inner support member 180 is shown comprising a hollow toroidal shaped distal or internal member. The distal retention member 180 is sized and configured to be insert-able through a small surgical incision and subsequently pressurized or inflated to achieve a preferred shape and size 180' that may not otherwise be insertable through the incision. A preferred embodiment may include an inflatable toroidal retention member 180 that is pressurized by gas or fluid by means of a gas or fluid supply associated with a transfer conduit 181. The unpressurized internal support member 180 may be easily placed through a small surgical incision and subsequently expanded, pressurized or filled to achieve preferred size or rigidity. A preferred embodiment of the inflatable member comprises a toroidal support element having a supply conduit that may be further connected to a syringe 182 having a preferred volume for gas or fluid. The inflatable member may be deflated at anytime for easy retrieval from the surgical incision.

Figure 21A:
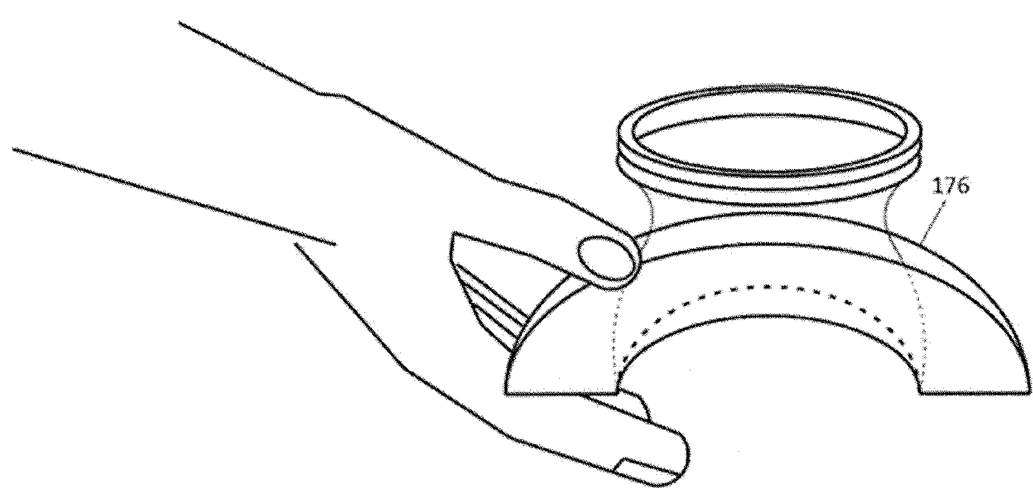
FIG. 21A illustrates a foldable inner support member of a circumferential retractor, having a disk-shaped inner support member shown in the folded position.
Figure 21B:
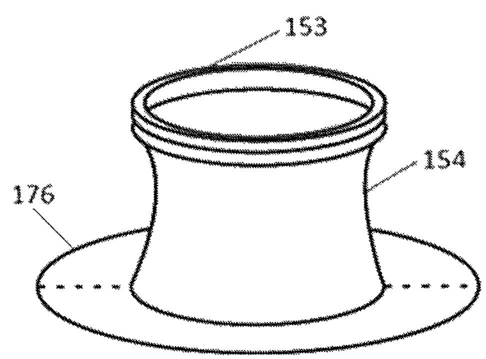
FIG. 21B illustrates the foldable inner support member of FIG. 21A, shown in an unfolded position.
Figure 21C:
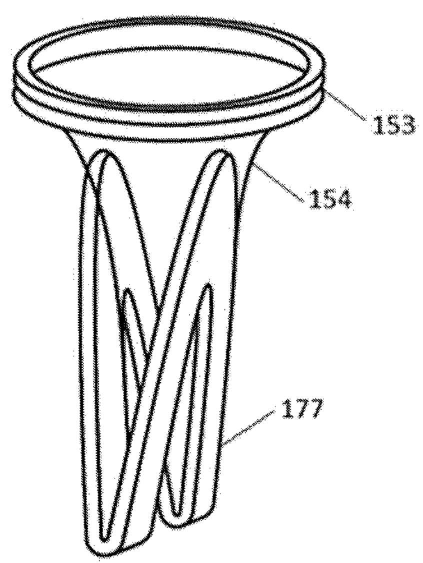
FIG. 21C illustrates a ring-shaped inner support member.

A further embodiment of an expandable inner support member may comprise a toroidal-shaped, disk-shaped 176 or ring-shaped 177 inner member constructed from "memory-foam". A preferred embodiment of memory foam may include the use of "viscoelastic" polyurethane foam. The viscoelastic foam element may be deformed by hand or by packaging, inserted through a surgical incision and subsequently allowed to return to a predetermined shape and size once within the surgical site. Embodiments of this design are shown in FIG. 21.

Referring to FIGS. 4, 6, 7, 9, 10, 22 and 23, the present invention contemplates several methods for creating operative space within an anatomical region. Using, as an example, a human breast 11, a first method for creating operative space may comprise: placing a circumferential retractor 71 within an incision, attaching at least a first manipulating or positioning element 90 upon a placed retractor 71 and maneuvering said positioning element 90 so as to create a working environment.

A second method for creating operative space may comprise: placing a circumferential retractor 71 within an incision, attaching a proximal or external seal member or cap 157 and supplying an insufflation gas to the associated body cavity. An additional method for creating operative space may further comprise a combination of the two previously described methods.

Figure 22A:
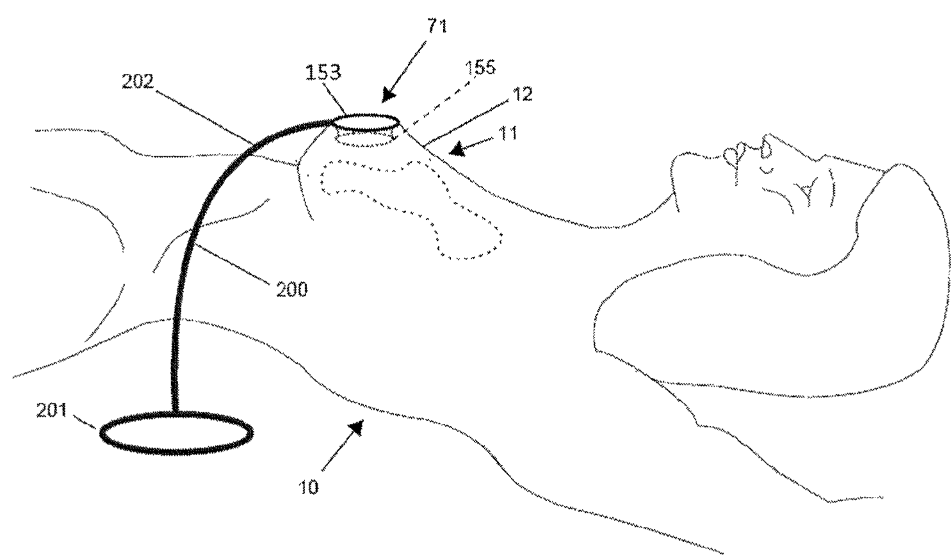
FIG. 22A shows a lateral view of a support member associated with a circumferential retractor, before manipulating the support member to increase the surgical field.
Figure 22B:
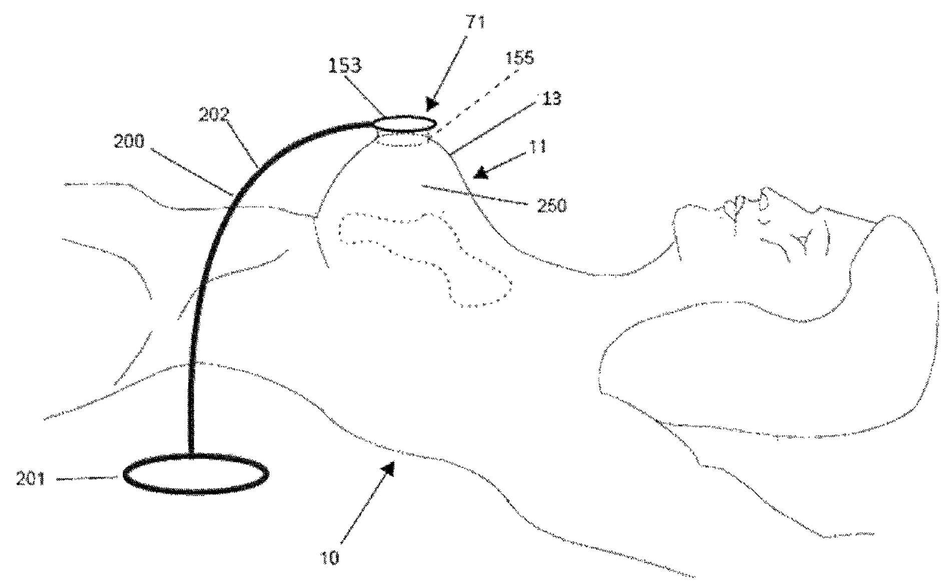
FIG. 22B shows a lateral view of a support member associated with a circumferential retractor, after manipulating the support member to increase the surgical field.

A further method for developing and maintaining an operative space, shown in FIG. 22, may include the use of an adjustable external support structures 200. For example, an adjustable structure may comprise a semi-flexible "goose-neck" type element 202 that provides sufficient support to prevent collapse of the surgical field 250. The adjustable structure detachably connects to the external support member 153 of the circumferential retractor 71 at a proximal end; the distal end comprises a table stand 201 that may be affixed to the operative table. As shown in FIG. 22A, after the circumferential retractor 71 is placed at the desired surgical site, the support structure 200 is attached to the external support member 153. The adjustable neck portion 202 of the structure 200 may be positionable by hand to, for example, raise the circumferential retractor 71, and thus the breast, to thereby expand the surgical field 250 (FIG. 22B). While adjustable, the neck does have sufficient stiffness to remain as positioned as the surgery continues.

Figure 23:
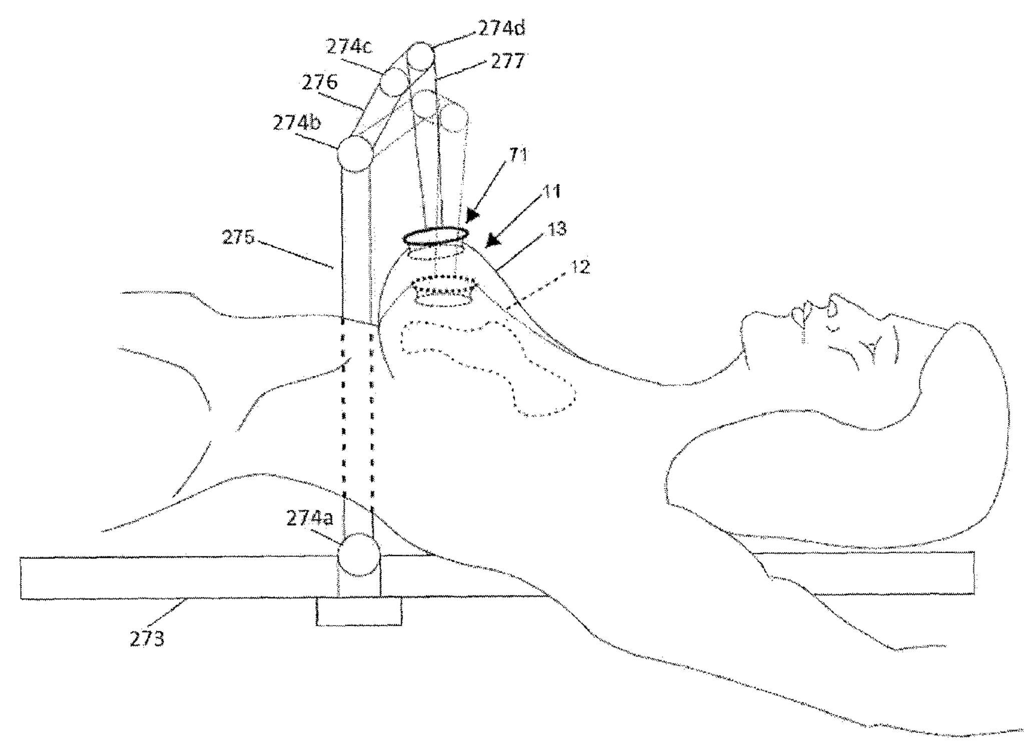
FIG. 23 illustrates the use of a hinged, pivoted support element attached to a circumferential retractor.

A more robust support structure, shown in FIG. 23, may comprise a hinged or pivoted arm 275. The pivot-points 274*a-d* may further comprise tensioning controls that maintain individual arm segments 275, 276, 277 as positioned. A preferred embodiment of the foregoing contemplates that the support structures 200, 275 may be attached to an operative table 273 or a stand. In FIG. 23, the breast 11 is shown in a first, unexpanded state 12, with the corresponding position of the hinged pivoted arm shown in broken lines, and in a second, expanded state 13, with the corresponding position of the hinged pivoted arm shown in solid lines.

Figure 24:
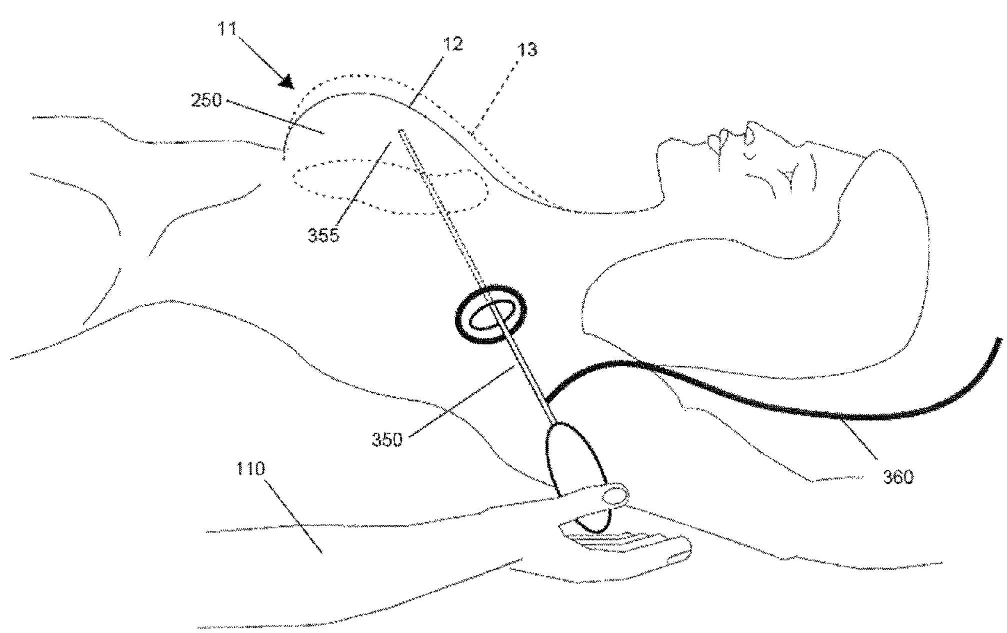
FIG. 24 illustrates the use of a dissecting tool having a gas or fluid supply.

Operative space is often increased using insufflation, wherein a gas, for example, is pumped into the operative field to thereby expand it. Insufflation is commonly used in abdominal procedures, where the relatively large abdominal chamber may safely accommodate, within a limited range, the accompanying changes in pressure. When operating in a smaller space, however, even small changes in pressure can pose risk when insufflating the operative field. Such an increase of internal pressure may occur when a gas or fluid dissection device is employed, such as the device shown in FIG. 24, in which gas or fluid is introduced into the surgical field 250 through the distal end 355 of an elongate laparoscopic instrument 350 attached to an insufflation gas or fluid conduit 360. Accordingly, the present invention optionally incorporates a safety check or pressure relief valve for use in insufflating smaller operative fields in regions like the breast.

Figure 25:
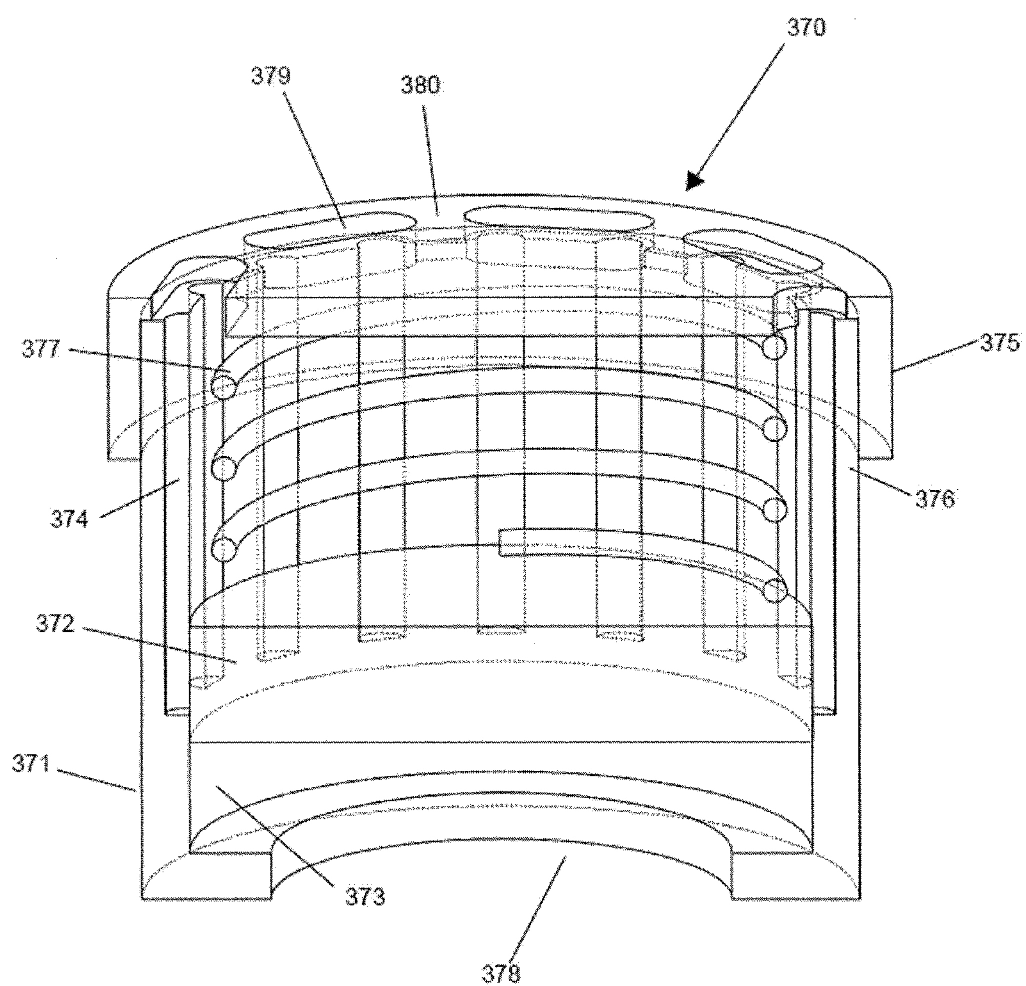
FIG. 25 is a side section view of a relief valve for use with a sealed circumferential retractor.
Figure 26:
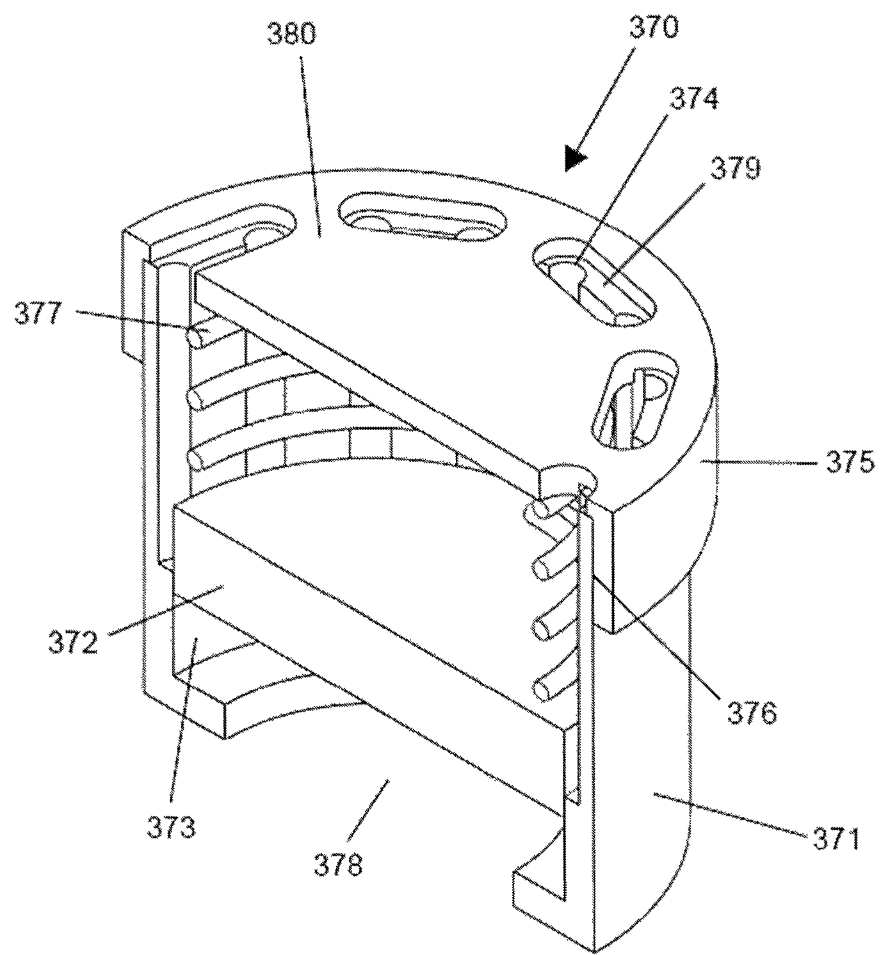
FIG. 26 is an oblique section view of a relief valve for use with a sealed circumferential retractor.

Referring to FIGS. 25 and 26, a preferred embodiment of a seal-cap 380 according to the present invention further contemplates a pressure sensitive relief-valve 370 associated with the insufflation gas supply. A preferred insufflation pressure is maintained as dissection gas or fluid is introduced into the body cavity or operative work-space. A preferred relief-valve 370 may include an adjustable spring-loaded mechanism sized and configured to respond to low pressure and small changes in pressure that may not be recognizable to a conventional insufflation gas supply. A preferred valve protects the operative cavity from over inflation beyond the capabilities of the insufflators. The valve 370 allows gas to escape if a predetermined pressure is exceeded.

A preferred relief valve 370 may comprise a cylindrical body 371, an adjustable cap 375, a compression spring 377 and an elastomeric seal 372. A cylindrical body 371 may include a structure having a smooth sealing, first surface 373, and a fenestrated second surface 374. As the elastomeric seal member 372 is forced upward against the compression spring 377 by internal gas pressure, the fenestrated second surface 374 allows gas to escape through a plurality of openings 379 in the adjustable cap 375. When pressure is returned to an appropriate level, the compression spring 377 returns the seal member 372 to the smooth, first, sealing portion 373 of the cylindrical body 371.

A further preferred embodiment comprises a cap 375 that is axially and radially adjustable so that the preferred gas pressure may be selected or adjusted by restriction of the orifices 374 and further by compression or decompression of the internal spring 377.

Figure 27:
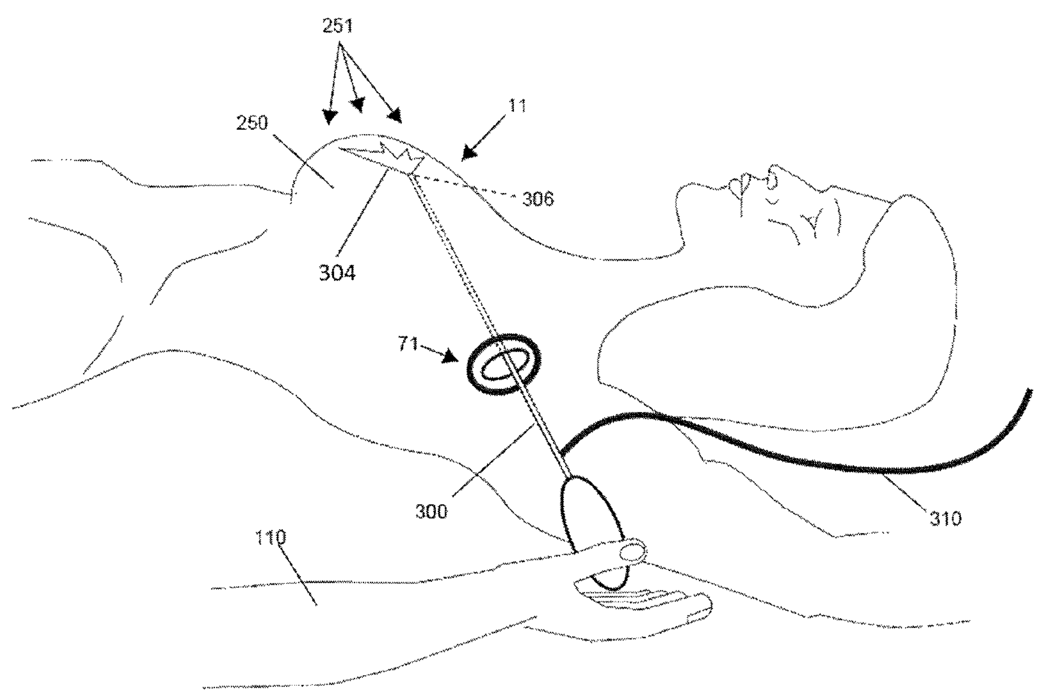
FIG. 27 illustrates the use of an illuminating instrument.

With reference to FIG. 27, the present invention further comprises, in combination with circumferential retraction in a human breast, a method for illuminating a portion of tissue within a developing cavity or work-space 250. The illumination may be useful for directly visualizing the activity of a mechanical dissector. In addition to direct visualization, the illumination may be an external indicator 251 of the internal activity or the position of an illuminated instrument 300 connected to a light source 310. In a preferred embodiment, a substantially flat or spatulated dissecting instrument may be provided for use in an insufflated cavity 250. The distal end 306 of the device 300 may further comprise a plurality of lumens. A first lumen may deliver a flow of gas. A second lumen may deliver a flow of liquid or a vacuum. A third lumen may contain a fiber optic element, light emitting diode or other illuminating element.

Figure 28:
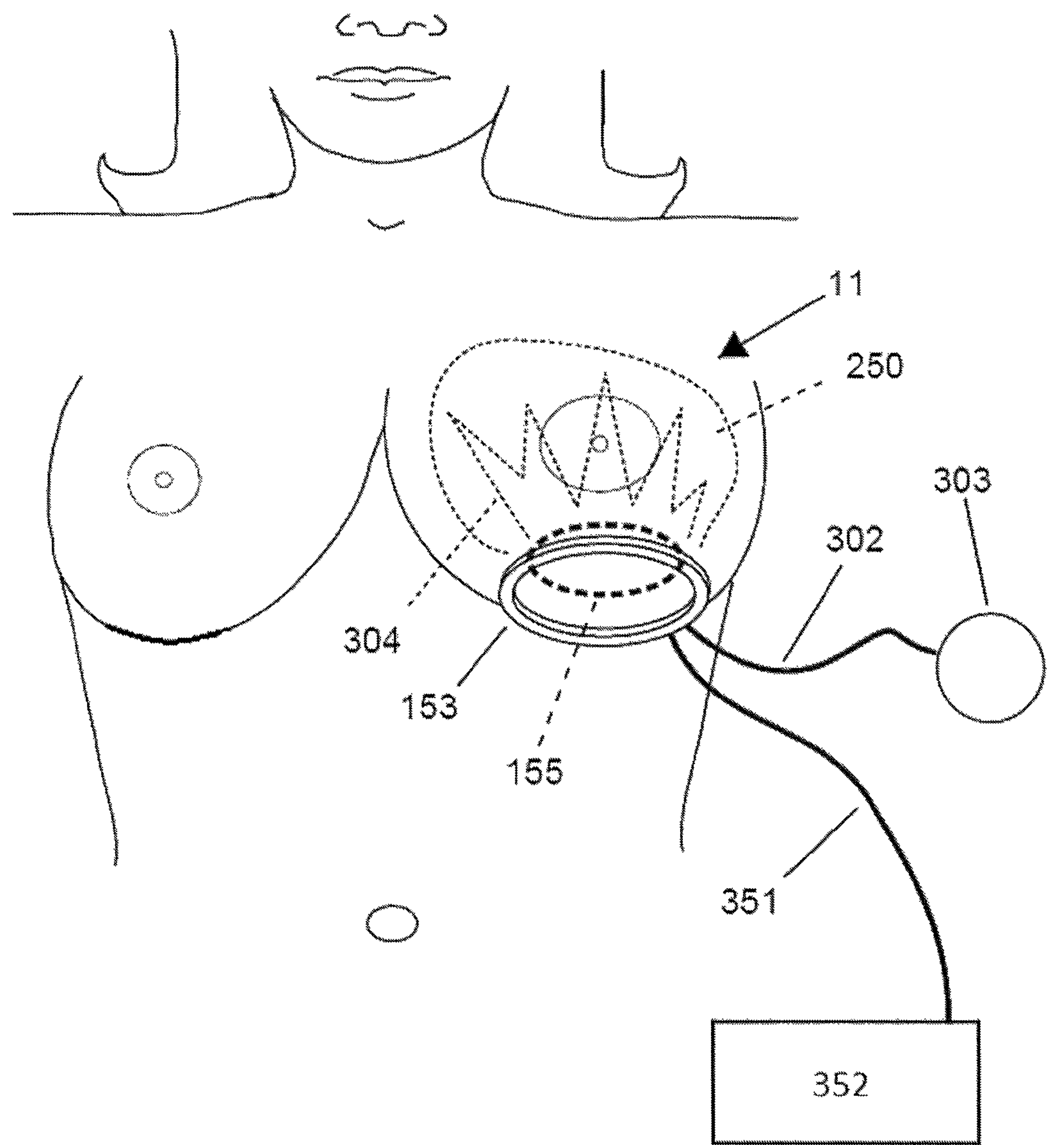
FIG. 28 illustrates a circumferential insufflating retractor having a seal-cap and an illuminating element.
Figure 29:
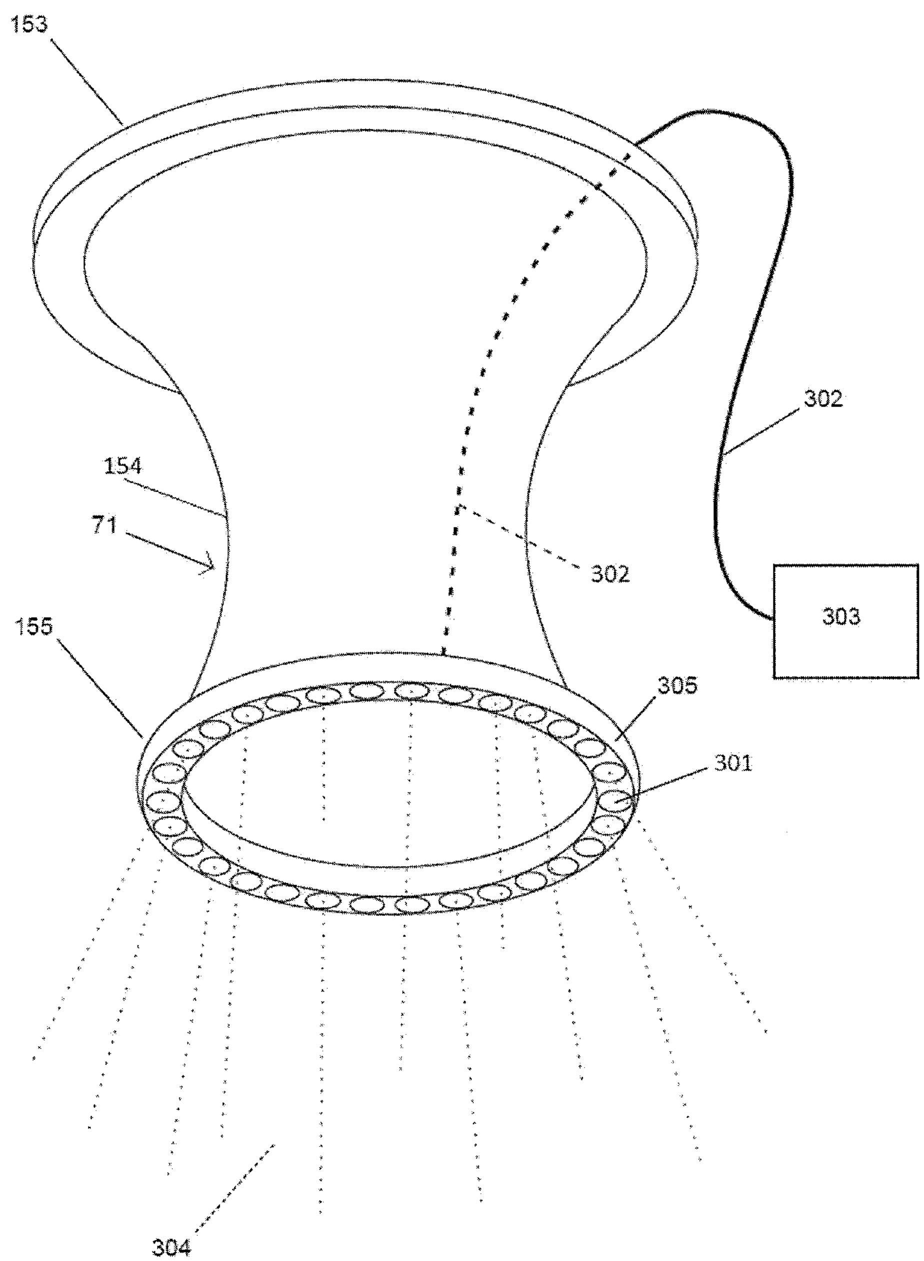
FIG. 29 is an enlarged oblique bottom-side view of a circumferential retractor having an integrated illuminating element.
Figure 30:
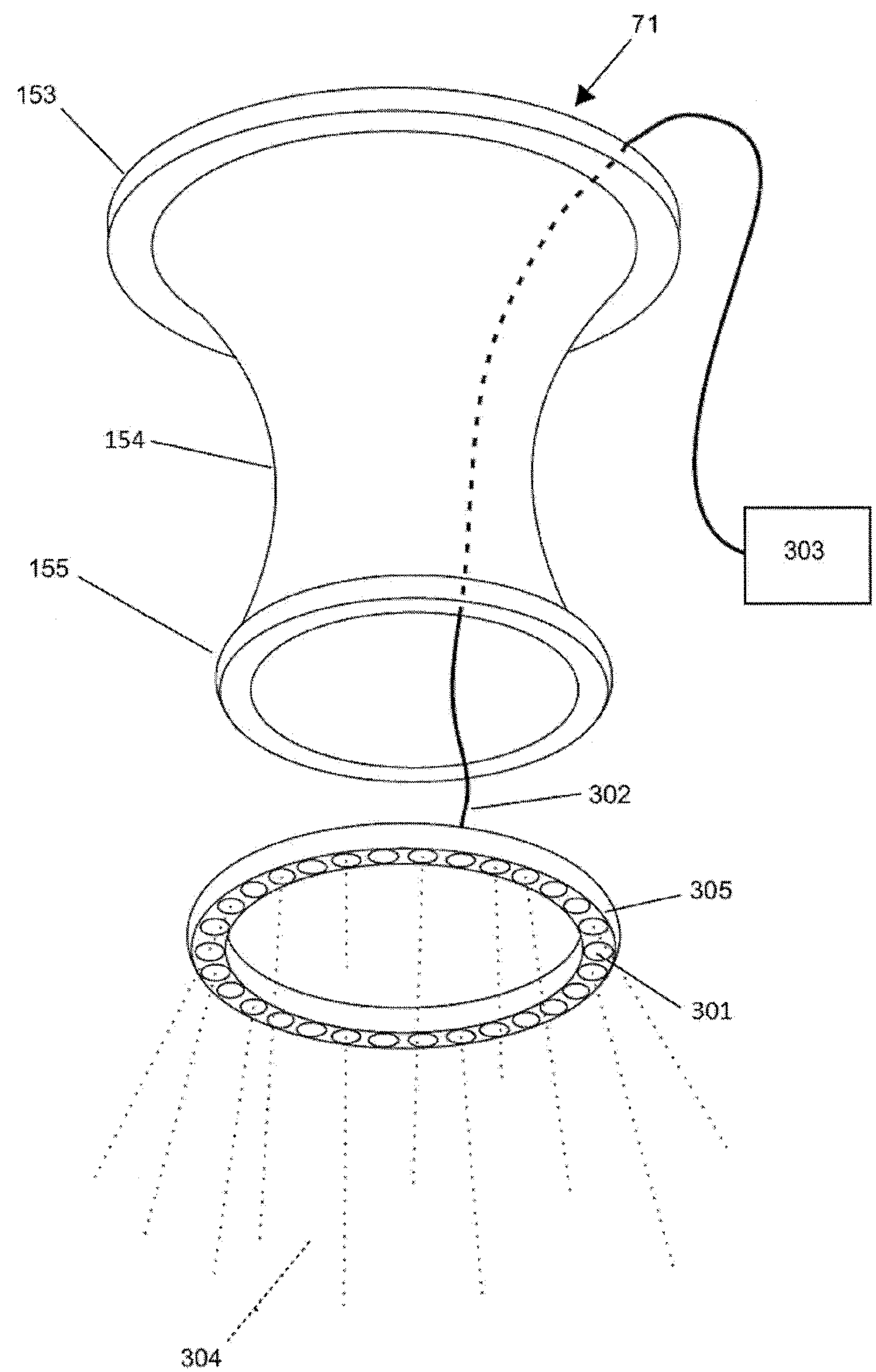
FIG. 30 is an exploded oblique bottom-side view of a circumferential retractor having a detachable illuminating element.

Now referring to FIGS. 28-30, a circumferential wound retractor according to the present invention may further comprise a rigid or semi-rigid, first, circular external support member 153 connected to a cylindrical, second, connecting member 154 that is further connected to a semi-rigid, circular, third, internal support member 155. A preferred embodiment provides an illumination element or elements that are associated with the internal support member 155. A preferred illumination element may comprise a flexible fiber-optic structure, a tubular ring having a plurality of light emitting diodes, a plurality of incandescent or fluorescent light sources or the like.

In use, the internal support member 155 may be inserted through an incision in a body wall and into a body cavity 250. Once in place, the illumination elements on the internal support member 155 may be energized to produce visible light 304 to illuminate a subject field or area of interest 250. An insufflation tube 351 attached to an insufflation gas source 352 may be used to insufflate the surgical site, with the illuminating internal member provides exceptional visual presence.

A preferred embodiment of an illumination element associated with the internal support member 155 of a circumferential wound retractor may comprise a transparent or opaque flexible tubular ring 305 having a circumferential lumen. The lumen may be packed with illuminating elements. Individual Light Emitting Diodes (LEDs) 301 may comprise a preferred embodiment in a flexible or semi-flexible tubular structure 305. A flexible fiber-optic bundle may comprise an alternate embodiment. The illumination element is connected to an illumination source 303 (a light source for fiberoptic cables or an energy source for LEDs) via a connecting member 302 (a fiber optic cable or an electrical conduit for energizing LEDs). Optionally, the tubular ring includes at least a partial reflective surface configured to reflect light into the operative field 250, facilitating the use of lower intensity lights and reducing the risk of overheating.

A further embodiment of the present invention may comprise a circumferential retractor having a distal, internal support member 155 sized and configured to receive and hold an illuminating member 305. An illuminating member 305 according to this embodiment may be attachable to and removable from, the internal support member 155 associated with the circumferential retractor.

While certain embodiments have been particularly shown and described with reference to exemplary embodiments thereof, it will be understood by those of ordinary skill in the art that various changes in form and details may be made therein without departing from the spirit and scope thereof as defined by the following claims.

What is claimed is:

1. A surgical retractor, comprising:

an external support member;

an internal support member;

a connecting member having a distal end, a proximal end, and a tissue contacting surface, the proximal end of the connecting member connected to the external support member and the distal end of the connecting member connected to the internal support member;

a first positioning element comprising a first holding portion and a first connecting portion, wherein the first connecting portion is releasably connected to the external support member; and a second positioning element, comprising a second holding portion and a second connecting portion, wherein the second connecting portion is releasably connected to the first connecting portion, wherein the first connecting portion defines a generally semicircular configuration adapted to slide under and engage the external support member, and wherein the first connecting portion further comprising a first engaging feature and the second connecting portion further comprising a second engaging feature, wherein the first engaging feature connects to the second engaging feature when the second connecting portion is disposed over the external support structure to thereby capture the external support structure between the first and second connecting portions.

2. The surgical retractor of claim 1, further comprising a support structure, the support structure having a base and a pivot point, wherein the base is configured to attach to a surgical table and the pivot point is configured to attach to the holding portion of at least one of the positioning elements.

3. The surgical retractor of claim 1, further comprising a first support structure and a second support structure, each support structure having a base and a pivot point, wherein the bases are configured to attach to a surgical table, the pivot point of the first support structure is attached to the first positioning element and the pivot point of the second support structure is attached to the second positioning element.

4. The surgical retractor of claim 1, wherein the internal support member comprises an inflatable toroid, the inflatable toroid being connected to a transfer conduit configured to interact with a gas or fluid supply.

5. The surgical retractor of claim 1, wherein the internal support member comprises a memory foam, the internal support member configured to be deformed for insertion through an incision, returning to a predetermined shape once within the surgical field.

6. The surgical retractor of claim 1, wherein the first engaging feature comprises detent and the second engaging feature comprises a tab.

7. The surgical retractor of claim 1, wherein the first engaging feature comprises lattice and the second engaging feature comprises a hook.

* * * * *